United States Patent
Haga et al.

(10) Patent No.: US 12,428,451 B2
(45) Date of Patent: Sep. 30, 2025

(54) IMMUNOGLOBULIN-BINDING PROTEIN, AND AFFINITY CARRIER USING SAME

(71) Applicants: JSR CORPORATION, Minato-ku (JP); JSR Life Sciences, LLC, Sunnyvale, CA (US); JSR MICRO N.V., Leuven (BE)

(72) Inventors: Tomoaki Haga, Minato-ku (JP); Takashi Ichii, Minato-ku (JP); Shunsuke Onogi, Minato-ku (JP); Satoshi Nakamura, Minato-ku (JP); Toshinari Honda, Minato-ku (JP); Tomoyuki Kamide, Minato-ku (JP)

(73) Assignees: JSR CORPORATION, Minato-ku (JP); JSR Life Sciences, LLC, Sunnyvale, CA (US); JSR MICRO N.V., Leuven (BE)

(*) Notice: Subject to any disclaimer, the term of this patent is extended or adjusted under 35 U.S.C. 154(b) by 1264 days.

(21) Appl. No.: 17/268,804

(22) PCT Filed: Aug. 23, 2019

(86) PCT No.: PCT/JP2019/033138
§ 371 (c)(1),
(2) Date: Feb. 16, 2021

(87) PCT Pub. No.: WO2020/040307
PCT Pub. Date: Feb. 27, 2020

(65) Prior Publication Data
US 2021/0179671 A1 Jun. 17, 2021

(30) Foreign Application Priority Data

Aug. 24, 2018 (JP) ................. 2018-157620
Apr. 8, 2019 (JP) ................. 2019-073529

(51) Int. Cl.
*C07K 14/31* (2006.01)
*B01D 15/38* (2006.01)
*C07K 1/22* (2006.01)
*C07K 16/00* (2006.01)

(52) U.S. Cl.
CPC .......... *C07K 14/31* (2013.01); *B01D 15/3809* (2013.01); *C07K 1/22* (2013.01); *C07K 16/00* (2013.01)

(58) Field of Classification Search
None
See application file for complete search history.

(56) References Cited

U.S. PATENT DOCUMENTS

| | | |
|---|---|---|
| 2005/0143566 A1 | 6/2005 | Hober |
| 2010/0221844 A1 | 9/2010 | Bian et al. |
| 2010/0286373 A1 | 11/2010 | Majima et al. |
| 2012/0149875 A1 | 6/2012 | Johansson et al. |
| 2014/0005357 A1 | 1/2014 | Nakamura et al. |
| 2014/0100356 A1 | 4/2014 | Yoshida et al. |
| 2016/0159855 A1 | 6/2016 | Rodrigo et al. |
| 2016/0215026 A1* | 7/2016 | Yoshida ................. C07K 14/31 |
| 2017/0333811 A1 | 11/2017 | Yoda et al. |
| 2017/0334954 A1 | 11/2017 | Rodrigo et al. |
| 2018/0044374 A1* | 2/2018 | Forss ..................... B01D 15/34 |
| 2019/0202871 A1 | 7/2019 | Shin et al. |

FOREIGN PATENT DOCUMENTS

| | | |
|---|---|---|
| EP | 3 255 058 A1 | 12/2017 |
| EP | 3 276 002 A1 | 1/2018 |
| JP | 2005-538693 A | 12/2005 |
| JP | 2007-252368 A | 10/2007 |
| JP | 2010-81866 A | 4/2010 |
| JP | 2010-156687 A | 7/2010 |
| JP | 2012-515160 A | 7/2012 |
| JP | 2014-508118 A | 4/2014 |
| JP | 2016-523959 A | 8/2016 |
| JP | 2017-533924 A | 11/2017 |
| WO | WO 00/23580 A1 | 4/2000 |
| WO | WO 03/080655 A1 | 10/2003 |
| WO | WO 2006/092338 A2 | 9/2006 |
| WO | WO 2007/067596 A2 | 6/2007 |
| WO | WO 2007/067596 A3 | 6/2007 |
| WO | WO 2012/033446 A1 | 3/2012 |
| WO | WO 2012/133342 A1 | 10/2012 |
| WO | WO 2013/109302 A2 | 7/2013 |
| WO | WO 2014/046278 A1 | 3/2014 |
| WO | WO 2015/034056 A1 | 3/2015 |

(Continued)

OTHER PUBLICATIONS

International Search Report issued on Oct. 8, 2019 in PCT/JP2019/033138 filed on Aug. 23, 2019, 4 pages.
Hober et al., "Protein A chromatography for antibody purification", Journal of Chromatography B, 2007, vol. 848, pp. 40-47.
Partial Supplementary European Search Report issued on Aug. 26, 2022, in corresponding European Patent Application No. 19851068.7, 17 pages.
Masoumeh Nosrati, et al., "Insights from engineering the Affibody-Fc interaction with a computational-experimental method", Protein Engineering, Design and Selection, vol. 30, No. 9, Sep. 1, 2017, pp. 593-601, XP55951625.

(Continued)

*Primary Examiner* — Changhwa J Cheu
(74) *Attorney, Agent, or Firm* — Oblon, McClelland, Maier & Neustadt, L.L.P.

(57) ABSTRACT

An affinity carrier may have improved alkali resistance. An immunoglobulin-binding protein containing a mutant polypeptide chain, as well as an affinity carrier containing a solid-phase carrier to which the immunoglobulin-binding protein is bound, may be a mutant polypeptide chain having an amino acid sequence having at least 85% identity to an amino acid sequence indicated by any of SEQ ID NO: 1-6 and 57-62, having a predetermined mutation, and having immunoglobulin-binding activity.

18 Claims, No Drawings
Specification includes a Sequence Listing.

(56) References Cited

FOREIGN PATENT DOCUMENTS

WO  WO 2016/125811 A1  8/2016
WO  WO 2018/009006 A1  1/2018

OTHER PUBLICATIONS

Elin Gunneriusson, et al., "Staphylococcal Surface Display of Immunoglobulin A (IgA)- and IgE-Specific In Vitro-Selected Binding Proteins (Affibodies) Based on *Staphylococcus aureus* Protein A", Applied and Environmental Microbiology, vol. 65, No. 9, Sep. 1, 1999, pp. 4134-4140, XP002966423.
Extended European Search Report issued Dec. 16, 2022 in European Patent Application No. 19851068.7, 17 pages.
Japanese Office Action issued on Jan. 24, 2023 in Japanese Patent Application 2020-538498, (with unedited computer-generated English translation), 29 pages.

* cited by examiner

IMMUNOGLOBULIN-BINDING PROTEIN, AND AFFINITY CARRIER USING SAME

TECHNICAL FIELD

The present invention relates to an immunoglobulin-binding protein, and an affinity carrier using the same, and to a method for isolating an antibody using the affinity carrier.

BACKGROUND ART

In recent years, antibodies have been widely used in, for example, reagents for research, and antibody drugs. These reagents and pharmaceutical antibodies are generally produced by purification using affinity chromatography. A column on which a ligand that is a substance specifically binding to immunoglobulin has been immobilized is used for affinity purification of antibodies, and an immunoglobulin-binding protein such as Protein A is generally used as the ligand.

Protein A is a cell wall protein derived from gram-positive bacteria *Staphylococcus aureus*. The Protein A has five immunoglobulin-binding domains called an E domain, a D domain, an A domain, a B domain, and a C domain, and each domain can bind alone to immunoglobulin. In addition to a natural-form immunoglobulin-binding domain of the Protein A, a modified immunoglobulin-binding domain to which protein engineering modification has been added is also utilized as a ligand for affinity purification.

A column for affinity purification of antibodies is usually washed with an alkaline solution and used repeatedly. However, since the natural-form immunoglobulin-binding domain of the Protein A has low alkali resistance, the antibody binding ability is largely lowered during repeated use in the column for affinity purification on which the natural-form domain is immobilized. In view of this, a modified Protein A domain having improved alkali resistance has been developed. For example, it is widely known that by substituting Gly at position 29 of an amino acid sequence of an immunoglobulin-binding domain of the Protein A with Ala, the chemical stability is improved (Non Patent Literature 1). Patent Literature 1 discloses a technique for improving alkali resistance of an immunoglobulin-binding domain by substituting Asn with an amino acid other than Gln and Cys or deleting Asn, in an amino acid sequence of the domain. Further, Patent Literature 2 discloses a technique for improving alkali resistance of a C, B or Z domain of Protein A by deleting three or more consecutive amino acids starting at position 1 or 2 from the N-terminus in the domain.

CITATION LIST

Patent Literature

Patent Literature 1: WO 2000/023580 A
Patent Literature 2: WO 2013/109302 A

Non Patent Literature

Non Patent Literature 1: Journal of Chromatography B, 2007, 848 (1): 40-47

SUMMARY OF INVENTION

Technical Problem

An affinity carrier having further improved alkali resistance has been demanded. The present invention is to provide an immunoglobulin-binding protein containing a mutant polypeptide chain having improved alkali resistance derived from an immunoglobulin-binding domain, and an affinity carrier using the immunoglobulin-binding protein. In addition, the present invention is to provide a method for isolating an antibody by using the affinity carrier.

Solution to Problem

The present invention provides the following ones.

[1] An immunoglobulin-binding protein, comprising a polypeptide chain consisting of an amino acid sequence having at least 85% identity to an amino acid sequence represented by any one of SEQ ID NOs: 1 to 6 and 57 to 62 and having at least one mutation selected from the group consisting of the following (a) to (f):

(a) substitution of an amino acid residue at at least one position selected from the group consisting of positions corresponding to positions 3, 6, and 11 of the amino acid sequence represented by SEQ ID NO: 3 with another amino acid residue, deletion of the amino acid residue at the at least one position, or insertion of another amino acid residue into a position in front of or behind the at least one position;

(b) substitution of an amino acid residue at at least one position selected from the group consisting of positions corresponding to positions 24 and 25 of the amino acid sequence represented by SEQ ID NO: 3 with another amino acid residue, deletion of the amino acid residue at the at least one position, or insertion of another amino acid residue into a position in front of or behind the at least one position;

(c) substitution of an amino acid residue at a position corresponding to position 39 of the amino acid sequence represented by SEQ ID NO: 3 with another amino acid residue, deletion of the amino acid residue at the position corresponding to position 39, or insertion of another amino acid residue into a position in front of or behind the position corresponding to position 39;

(d) substitution of an amino acid residue at a position corresponding to position 46 of the amino acid sequence represented by SEQ ID NO: 3 with another amino acid residue, deletion of the amino acid residue at the position corresponding to position 46, or insertion of another amino acid residue into a position in front of or behind the position corresponding to position 46;

(e) substitution of an amino acid residue at at least one position selected from the group consisting of positions corresponding to positions 4, 49, and 58 of the amino acid sequence represented by SEQ ID NO: 3 with another amino acid residue, deletion of the amino acid residue at the at least one position, or insertion of another amino acid residue into a position in front of or behind the at least one position; and (f) substitution of an amino acid residue at a position corresponding to position 23 of the amino acid sequence represented by SEQ ID NO: 3 with another amino acid residue, deletion of the amino acid residue at the position corresponding to position 23, or insertion of another amino acid residue into a position in front of or behind the position corresponding to position 23.

[2] The immunoglobulin-binding protein described in [1], wherein the polypeptide chain is a polypeptide chain consisting of an amino acid sequence having at least 85% identity to the amino acid sequence represented by SEQ ID NO: 3 and having at least one mutation selected from the group consisting of the above (a) to (f).

[3] The immunoglobulin-binding protein described in [1] or [2], wherein the at least one mutation selected from the group consisting of the above (a) to (f) is at least one mutation selected from the group consisting of:

($a_1$) substitution of Asn with Gln at a position corresponding to position 3 of the amino acid sequence represented by SEQ ID NO: 3;

($a_2$) substitution of Asn with Ala at a position corresponding to position 3 of the amino acid sequence represented by SEQ ID NO: 3;

($a_3$) substitution of Asn with Asp at a position corresponding to position 3 of the amino acid sequence represented by SEQ ID NO: 3;

($a_4$) substitution of Asn with Gln at a position corresponding to position 6 of the amino acid sequence represented by SEQ ID NO: 3;

($a_5$) substitution of Asn with Ala at a position corresponding to position 6 of the amino acid sequence represented by SEQ ID NO: 3;

($a_6$) substitution of Asn with Asp at a position corresponding to position 6 of the amino acid sequence represented by SEQ ID NO: 3;

($a_7$) substitution of Asn with Gln at a position corresponding to position 11 of the amino acid sequence represented by SEQ ID NO: 3;

($a_8$) substitution of Asn with Ala at a position corresponding to position 11 of the amino acid sequence represented by SEQ ID NO: 3;

($a_9$) substitution of Asn with Arg at a position corresponding to position 11 of the amino acid sequence represented by SEQ ID NO: 3;

($a_{10}$) substitution of Asn with Asp at a position corresponding to position 11 of the amino acid sequence represented by SEQ ID NO: 3;

($a_{11}$) substitution of Asn with Cys at a position corresponding to position 11 of the amino acid sequence represented by SEQ ID NO: 3;

($a_{12}$) substitution of Asn with Glu at a position corresponding to position 11 of the amino acid sequence represented by SEQ ID NO: 3;

($a_{13}$) substitution of Asn with His at a position corresponding to position 11 of the amino acid sequence represented by SEQ ID NO: 3;

($a_{14}$) substitution of Asn with Ile at a position corresponding to position 11 of the amino acid sequence represented by SEQ ID NO: 3;

($a_{15}$) substitution of Asn with Leu at a position corresponding to position 11 of the amino acid sequence represented by SEQ ID NO: 3;

($a_{16}$) substitution of Asn with Lys at a position corresponding to position 11 of the amino acid sequence represented by SEQ ID NO: 3;

($a_{17}$) substitution of Asn with Met at a position corresponding to position 11 of the amino acid sequence represented by SEQ ID NO: 3;

($a_{18}$) substitution of Asn with Phe at a position corresponding to position 11 of the amino acid sequence represented by SEQ ID NO: 3;

($a_{19}$) substitution of Asn with Thr at a position corresponding to position 11 of the amino acid sequence represented by SEQ ID NO: 3;

($a_{20}$) substitution of Asn with Trp at a position corresponding to position 11 of the amino acid sequence represented by SEQ ID NO: 3;

($a_{21}$) substitution of Asn with Tyr at a position corresponding to position 11 of the amino acid sequence represented by SEQ ID NO: 3;

($a_{22}$) substitution of Asn with Val at a position corresponding to position 11 of the amino acid sequence represented by SEQ ID NO: 3;

($b_1$) substitution of Glu with Asp at a position corresponding to position 24 of the amino acid sequence represented by SEQ ID NO: 3;

(b2) substitution of Glu with Asp at a position corresponding to position 25 of the amino acid sequence represented by SEQ ID NO: 3;

($c_1$) substitution of Ser with Lys at a position corresponding to position 39 of the amino acid sequence represented by SEQ ID NO: 3;

($c_2$) substitution of Ser with Arg at a position corresponding to position 39 of the amino acid sequence represented by SEQ ID NO: 3;

($d_1$) substitution of Ala with Asp at a position corresponding to position 46 of the amino acid sequence represented by SEQ ID NO: 3;

($d_2$) substitution of Ala with Glu at a position corresponding to position 46 of the amino acid sequence represented by SEQ ID NO: 3;

($d_3$) substitution of Ala with Lys at a position corresponding to position 46 of the amino acid sequence represented by SEQ ID NO: 3;

($d_4$) substitution of Ala with Arg at a position corresponding to position 46 of the amino acid sequence represented by SEQ ID NO: 3;

($e_1$) deletion of Lys at a position corresponding to position 4 of the amino acid sequence represented by SEQ ID NO: 3;

($e_2$) substitution of Lys with Arg at a position corresponding to position 49 of the amino acid sequence represented by SEQ ID NO: 3;

($e_3$) deletion of Lys at a position corresponding to position 58 of the amino acid sequence represented by SEQ ID NO: 3;

($e_4$) substitution of Lys with Arg at a position corresponding to position 58 of the amino acid sequence represented by SEQ ID NO: 3;

($f_1$) substitution of Thr with Arg at a position corresponding to position 23 of the amino acid sequence represented by SEQ ID NO: 3;

($f_2$) substitution of Thr with Leu at a position corresponding to position 23 of the amino acid sequence represented by SEQ ID NO: 3; and ($f_3$) substitution of Thr with Ser at a position corresponding to position 23 of the amino acid sequence represented by SEQ ID NO: 3.

[4] The immunoglobulin-binding protein described in [3], wherein the at least one mutation selected from the group consisting of the above (a) to (f) is any one of:

($a_1$) substitution of Asn with Gln at a position corresponding to position 3 of the amino acid sequence represented by SEQ ID NO: 3;

($a_2$) substitution of Asn with Ala at a position corresponding to position 3 of the amino acid sequence represented by SEQ ID NO: 3;

($a_3$) substitution of Asn with Asp at a position corresponding to position 3 of the amino acid sequence represented by SEQ ID NO: 3;

($a_4$) substitution of Asn with Gln at a position corresponding to position 6 of the amino acid sequence represented by SEQ ID NO: 3;

($a_5$) substitution of Asn with Ala at a position corresponding to position 6 of the amino acid sequence represented by SEQ ID NO: 3;
($a_6$) substitution of Asn with Asp at a position corresponding to position 6 of the amino acid sequence represented by SEQ ID NO: 3;
($a_7$) substitution of Asn with Gln at a position corresponding to position 11 of the amino acid sequence represented by SEQ ID NO: 3;
($a_8$) substitution of Asn with Ala at a position corresponding to position 11 of the amino acid sequence represented by SEQ ID NO: 3;
($a_9$) substitution of Asn with Arg at a position corresponding to position 11 of the amino acid sequence represented by SEQ ID NO: 3;
($a_{10}$) substitution of Asn with Asp at a position corresponding to position 11 of the amino acid sequence represented by SEQ ID NO: 3;
($a_{11}$) substitution of Asn with Cys at a position corresponding to position 11 of the amino acid sequence represented by SEQ ID NO: 3;
($a_{12}$) substitution of Asn with Glu at a position corresponding to position 11 of the amino acid sequence represented by SEQ ID NO: 3;
($a_{13}$) substitution of Asn with His at a position corresponding to position 11 of the amino acid sequence represented by SEQ ID NO: 3;
($a_{14}$) substitution of Asn with Ile at a position corresponding to position 11 of the amino acid sequence represented by SEQ ID NO: 3;
($a_{15}$) substitution of Asn with Leu at a position corresponding to position 11 of the amino acid sequence represented by SEQ ID NO: 3;
($a_{16}$) substitution of Asn with Lys at a position corresponding to position 11 of the amino acid sequence represented by SEQ ID NO: 3;
($a_{17}$) substitution of Asn with Met at a position corresponding to position 11 of the amino acid sequence represented by SEQ ID NO: 3;
($a_{18}$) substitution of Asn with Phe at a position corresponding to position 11 of the amino acid sequence represented by SEQ ID NO: 3;
($a_{19}$) substitution of Asn with Thr at a position corresponding to position 11 of the amino acid sequence represented by SEQ ID NO: 3;
($a_{20}$) substitution of Asn with Trp at a position corresponding to position 11 of the amino acid sequence represented by SEQ ID NO: 3;
($a_{21}$) substitution of Asn with Tyr at a position corresponding to position 11 of the amino acid sequence represented by SEQ ID NO: 3;
($a_{22}$) substitution of Asn with Val at a position corresponding to position 11 of the amino acid sequence represented by SEQ ID NO: 3;
($a_{23}$) substitution of Asns with Glns at positions corresponding to positions 3, 6, and 11 of the amino acid sequence represented by SEQ ID NO: 3;
($a_{24}$) substitution of Asn with Ala at a position corresponding to position 3 and substitution of Asn with Gln at a position corresponding to position 11, of the amino acid sequence represented by SEQ ID NO: 3;
($a_{25}$) substitution of Asn with Asp at a position corresponding to position 3 and substitution of Asn with Gln at a position corresponding to position 11, of the amino acid sequence represented by SEQ ID NO: 3;
($a_{26}$) substitution of Asn with Asp at a position corresponding to position 6 and substitution of Asn with Gln at a position corresponding to position 11, of the amino acid sequence represented by SEQ ID NO: 3;
($a_{27}$) substitution of Asn with Asp at a position corresponding to position 3, substitution of Asn with Asp at a position corresponding to position 6, and substitution of Asn with Gln at a position corresponding to position 11, of the amino acid sequence represented by SEQ ID NO: 3;
($a_{28}$) substitution of Asn with Ala at a position corresponding to position 3, substitution of Asn with Asp at a position corresponding to position 6, and substitution of Asn with Gln at a position corresponding to position 11, of the amino acid sequence represented by SEQ ID NO: 3;
($b_1$) substitution of Glu with Asp at a position corresponding to position 24 of the amino acid sequence represented by SEQ ID NO: 3;
($b_2$) substitution of Glu with Asp at a position corresponding to position 25 of the amino acid sequence represented by SEQ ID NO: 3;
($c_1$) substitution of Ser with Lys at a position corresponding to position 39 of the amino acid sequence represented by SEQ ID NO: 3;
($c_2$) substitution of Ser with Arg at a position corresponding to position 39 of the amino acid sequence represented by SEQ ID NO: 3;
($d_1$) substitution of Ala with Asp at a position corresponding to position 46 of the amino acid sequence represented by SEQ ID NO: 3;
($d_2$) substitution of Ala with Glu at a position corresponding to position 46 of the amino acid sequence represented by SEQ ID NO: 3;
($d_3$) substitution of Ala with Lys at a position corresponding to position 46 of the amino acid sequence represented by SEQ ID NO: 3;
($d_4$) substitution of Ala with Arg at a position corresponding to position 46 of the amino acid sequence represented by SEQ ID NO: 3;
($e_1$) deletion of Lys at a position corresponding to position 4 of the amino acid sequence represented by SEQ ID NO: 3;
($e_2$) substitution of Lys with Arg at a position corresponding to position 49 of the amino acid sequence represented by SEQ ID NO: 3;
($e_3$) deletion of Lys at a position corresponding to position 58 of the amino acid sequence represented by SEQ ID NO: 3;
($e_4$) substitution of Lys with Arg at a position corresponding to position 58 of the amino acid sequence represented by SEQ ID NO: 3;
($f_1$) substitution of Thr with Arg at a position corresponding to position 23 of the amino acid sequence represented by SEQ ID NO: 3;
($f_2$) substitution of Thr with Leu at a position corresponding to position 23 of the amino acid sequence represented by SEQ ID NO: 3;
($f_3$) substitution of Thr with Ser at a position corresponding to position 23 of the amino acid sequence represented by SEQ ID NO: 3;
($g_1$) a combination of ($a_7$) and ($f_1$);
($g_2$) a combination of ($a_7$) and ($f_2$);
($g_3$) a combination of ($a_7$) and ($f_3$);
($g_4$) a combination of ($a_7$) and ($e_2$);
($g_5$) a combination of ($a_7$) and ($e_4$);
($g_6$) a combination of ($a_7$), ($f_1$), and ($e_2$);
($g_7$) a combination of ($a_7$), ($f_2$), and ($e_2$); and
($g_8$) a combination of ($a_7$), ($f_3$), and ($e_2$).

[5] The immunoglobulin-binding protein described in any one of [1] to [4], wherein the at least one mutation selected from the group consisting of the above (a) to (f) comprises substitution of amino acid residues at positions corresponding to at least two of positions 3, 6, 11, 24, 25, 39, 46, 4, 49, 58, and 23 of the amino acid sequence represented by SEQ ID NO: 3 with other amino acid residues, deletion of the amino acid residues at the positions, or insertion of other amino acid residues into positions in front of or behind the positions.

[6] The immunoglobulin-binding protein described in [5], wherein the at least one mutation is any one of the ($a_{23}$) to ($a_{28}$), or a combination of any one of the ($a_1$) to ($a_{20}$) and any one or more of the ($b_1$) to ($f_3$).

[7] The immunoglobulin-binding protein described in any one of [1] to [6], wherein the identity of the amino acid sequence is at least 90%.

[8] The immunoglobulin-binding protein described in any one of [1] to [7], wherein the polypeptide chain further contains substitution of an amino acid residue at a position corresponding to position 1 of the amino acid sequence represented by SEQ ID NO: 3 with Val and/or substitution of an amino acid residue at a position corresponding to position 29 of the amino acid sequence represented by SEQ ID NO: 3 with Ala.

[9] The immunoglobulin-binding protein described in any one of [1] to [8], wherein two or more of the polypeptide chains are contained.

[10] A polynucleotide encoding the immunoglobulin-binding protein described in any one of [1] to [9].

[11] A vector comprising the polynucleotide described in [10].

[12] A transformant comprising the vector described in [11].

[13] An affinity carrier comprising a solid carrier, and the immunoglobulin-binding protein described in any one of [1] to [9] bound to the solid carrier.

[14] A chromatography column comprising the affinity carrier of [13].

[15] A method for isolating an antibody or a fragment thereof, using the affinity carrier described in [13] or the chromatography column described in [14].

[16] A method for producing an immunoglobulin-binding protein, comprising expressing the immunoglobulin-binding protein described in any one of [1] to [9] in the transformant described in [12] or a cell-free protein synthesis system, or chemically synthesizing the immunoglobulin-binding protein.

[17] A method for producing a mutant polypeptide chain, comprising introducing at least one mutation into a polypeptide chain consisting of an amino acid sequence represented by any one of SEQ ID NOs: 1 to 6 and 57 to 62 or an amino acid sequence having at least 85% identity to the amino acid sequence represented by any one of SEQ ID NOs: 1 to 6 and 57 to 62 and further having immunoglobulin-binding activity, wherein the at least one mutation is selected from the group consisting of the following (a) to (f):

(a) substitution of an amino acid residue at at least one position selected from the group consisting of positions corresponding to positions 3, 6, and 11 of the amino acid sequence represented by SEQ ID NO: 3 with another amino acid residue, deletion of the amino acid residue at the at least one position, or insertion of another amino acid residue into a position in front of or behind the at least one position;

(b) substitution of an amino acid residue at at least one position selected from the group consisting of positions corresponding to positions 24 and 25 of the amino acid sequence represented by SEQ ID NO: 3 with another amino acid residue, deletion of the amino acid residue at the at least one position, or insertion of another amino acid residue into a position in front of or behind the at least one position;

(c) substitution of an amino acid residue at a position corresponding to position 39 of the amino acid sequence represented by SEQ ID NO: 3 with another amino acid residue, deletion of the amino acid residue at the position corresponding to position 39, or insertion of another amino acid residue into a position in front of or behind the position corresponding to position 39;

(d) substitution of an amino acid residue at a position corresponding to position 46 of the amino acid sequence represented by SEQ ID NO: 3 with another amino acid residue, deletion of the amino acid residue at the position corresponding to position 46, or insertion of another amino acid residue into a position in front of or behind the position corresponding to position 46;

(e) substitution of an amino acid residue at at least one position selected from the group consisting of positions corresponding to positions 4, 49, and 58 of the amino acid sequence represented by SEQ ID NO: 3 with another amino acid residue, deletion of the amino acid residue at the at least one position, or insertion of another amino acid residue into a position in front of or behind the at least one position; and (f) substitution of an amino acid residue at a position corresponding to position 23 of the amino acid sequence represented by SEQ ID NO: 3 with another amino acid residue, deletion of the amino acid residue at the position corresponding to position 23, or insertion of another amino acid residue into a position in front of or behind the position corresponding to position 23.

[18] A method for producing an affinity carrier, comprising immobilizing the immunoglobulin-binding protein described in any one of [1] to [9] on a solid carrier.

Advantageous Effects of Invention

The mutant polypeptide chain of the present invention, and an immunoglobulin-binding protein containing the mutant polypeptide chain have immunoglobulin binding, and further have improved alkali resistance. Accordingly, the immunoglobulin-binding protein according to the present invention is useful as an affinity ligand. The affinity carrier according to the present invention, on which the immunoglobulin-binding protein has been immobilized, can maintain the immunoglobulin-binding activity even after repeated washing (cleaning-in-place, hereinafter also referred to as CIP) using an alkaline solution.

DESCRIPTION OF EMBODIMENTS

In the present specification, the identity of an amino acid sequence and a nucleotide sequence can be determined by using the algorithm BLAST by Karlin and Altschul (Pro. Natl. Acad. Sci. USA, 1993, 90: 5873-5877). On the basis of the BLAST algorithm, programs called BLASTN, BLASTX, BLASTP, TBLASTN, and TBLASTX have been developed (J. Mol. Biol., 1990, 215: 403-410). In a case where these programs are used, a default parameter of each program can be used. Specific techniques of these analysis methods are known (see [www.ncbi.nlm.nih.gov]).

In the present specification, the expression "at least 85% identity" concerning an amino acid sequence and an nucleotide sequence refers to 85% or more identity, preferably 90% or more identity, more preferably 95% or more identity, furthermore preferably 97% or more identity, still furthermore preferably 98% or more identity, and even still more preferably 99% or more identity. Further, the expression "at least 90% identity" concerning an amino acid sequence and a nucleotide sequence refers to 90% or more identity, preferably 95% or more identity, furthermore preferably 97% or more identity, still furthermore preferably 98% or more identity, and even still more preferably 99% or more identity.

In the present specification, the "positions corresponding to positions" on an amino acid sequence and an nucleotide sequence can be determined each with the alignment of a target sequence and a reference sequence (for example, the amino acid sequence represented by SEQ ID NO: 3) so that the maximum homology is given to the conserved amino acid residue or nucleotide which is present in the amino acid sequence or the nucleotide sequence. The alignment can be executed by using known algorithms, and the procedure is known to a person skilled in the art. For example, the alignment can be performed by using Clustal W multiple alignment program (Thompson, J. D. et al, 1994, Nucleic Acids Res., 22: 4673-4680) with the default settings. Clustal W can be used on the website of, for example, European Bioinformatics Institute (EBI [www.ebi.ac.uk/index.html]), or DNA Data Bank of Japan run by National Institute of Genetics (DDBJ [www.ddbj.nig.ac.jp/index.html]).

In the present specification, amino acid residues are also described in the following abbreviations: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), valine (Val or V), and any amino acid residue (Xaa or X). Further, in the present specification, the amino acid sequence of a peptide is described such that the amino terminus (hereinafter referred to as N-terminus) is located on the left side and the carboxyl terminus (hereinafter referred to as C-terminus) is located on the right side, in accordance with a routine procedure.

In the present specification, the positions "before" and "after" to a specific position of an amino acid sequence refer to positions adjacent on the N-terminal side and the C-terminal side of the specific position, respectively. For example, in a case where amino acid residues are inserted into the positions "before" and "after" a specific position, the amino acid residues after insertion are arranged at positions adjacent on the N-terminal side and the C-terminal side of the specific position, respectively.

In the present specification, the expression "immunoglobulin-binding protein" refers to a protein having binding activity to an antibody or a fragment of the antibody. The "antibody" in the present specification can include, for example, IgG, IgA, IgD, IgE, and IgM, and immunoglobulin in any class of subclasses of the IgG, IgA, IgD, IgE, and IgM, fragments thereof, and mutants thereof. Further, the "antibody" in the present specification may also be, for example, a chimeric antibody such as a humanized antibody, an antibody complex, and other immunoglobulin modifications containing an antigen recognition site. In addition, the "fragment of the antibody" in the present specification may be a fragment of an antibody containing an antigen recognition site, or may be a fragment of an antibody containing no antigen recognition site. Examples of the fragment of an antibody containing no antigen recognition site include a protein consisting only of the Fc region of immunoglobulin, a Fc fusion protein, and a mutant or modification of the protein or Fc fusion protein.

The expression "immunoglobulin-binding domain" in the present specification refers to a functional unit of a polypeptide that is contained in an immunoglobulin-binding protein and has binding activity of immunoglobulin (or an antibody or a fragment of an antibody). Preferable examples of the "immunoglobulin-binding domain" include an immunoglobulin-binding domain of Protein A, and a mutant of the domain having immunoglobulin-binding activity.

1. Immunoglobulin-Binding Protein

The immunoglobulin-binding protein according to the present invention contains at least one mutant polypeptide chain derived from an immunoglobulin-binding domain of Protein A of *Staphylococcus aureus* (hereinafter, also referred to as SpA). The mutant polypeptide chain contained in the immunoglobulin-binding protein according to the present invention is a polypeptide chain having immunoglobulin-binding activity, and is also referred to as the "mutant immunoglobulin-binding domain of the present invention" in the following present specification. The mutant immunoglobulin-binding domain of the present invention can be obtained by adding a predetermined mutation to an immunoglobulin-binding domain derived from SpA, which is the parent domain, or a mutant of the domain. The mutant immunoglobulin-binding domain of the present invention has immunoglobulin-binding activity, and further has improved alkali resistance as compared with that of the parent domain. The immunoglobulin-binding protein according to the present invention, which contains the mutant immunoglobulin-binding domain of the present invention, can be used as a ligand of an affinity carrier.

Examples of the parent domain of the mutant immunoglobulin-binding domain of the present invention include an immunoglobulin-binding domain of SpA, for example, an A domain, a B domain, a C domain, a D domain, an E domain, or a Z domain that is a modified domain of the B domain, and mutants of such domains. Among them, the B domain, the Z domain, the C domain, and the mutants of those domains are preferable, and the C domain, and the mutant of the C domain are more preferable.

The B domain, Z domain, C domain, D domain, A domain, and E domain of SpA, and the mutants of those domains can be used as parent domains of the mutant immunoglobulin-binding domain of the present invention. The B domain of SpA is a polypeptide chain consisting of an amino acid sequence represented by SEQ ID NO: 1. An example of the mutant of the B domain includes a polypeptide chain that consists of an amino acid sequence having at least 85% identity to the amino acid sequence represented by SEQ ID NO: 1 and further has immunoglobulin-binding activity. The Z domain of SpA is a polypeptide chain consisting of an amino acid sequence represented by SEQ ID NO: 2. An example of the mutant of the Z domain includes a polypeptide chain that consists of an amino acid sequence having at least 85% identity to the amino acid sequence represented by SEQ ID NO: 2 and further has immunoglobulin-binding activity. The C domain of SpA is a polypeptide chain consisting of an amino acid sequence represented by SEQ ID NO: 3. An example of the mutant of the C domain includes a polypeptide chain that consists of an amino acid sequence having at least 85% identity to the amino acid sequence represented by SEQ ID NO: 3 and further has immunoglobulin-binding activity. The D domain of SpA is a polypeptide chain consisting of an amino acid sequence represented by SEQ ID NO: 4. An example of the mutant of the D domain includes a polypeptide chain that consists of an amino acid sequence having at least 85% identity to the amino acid sequence represented by SEQ ID NO: 4 and further has immunoglobulin-binding activity. The A domain of SpA is a polypeptide chain consisting of an amino acid sequence represented by SEQ ID NO: 5. An example of the mutant of the A domain includes a polypeptide chain that consists of an amino acid sequence having at least 85% identity to the amino acid sequence represented by SEQ ID NO: 5 and further has immunoglobulin-binding activity. The E domain of SpA is a polypeptide chain consisting of an amino acid sequence represented by SEQ ID NO: 6. An example of the mutant of the E domain includes a polypeptide chain that consists of an amino acid sequence having at least 85% identity to the amino acid sequence represented by SEQ ID NO: 6 and further has immunoglobulin-binding activity.

Accordingly, examples of the preferable parent domain in the present invention include a polypeptide chain consisting of an amino acid sequence represented by any one of SEQ ID NOs: 1 to 6, and a polypeptide chain that consists of an amino acid sequence having at least 85% identity to the amino acid sequence represented by any one of SEQ ID NOs: 1 to 6 and further has immunoglobulin-binding activity. Examples of the more preferable parent domain include a polypeptide chain consisting of an amino acid sequence represented by any one of SEQ ID NOs: 1 to 3, and a polypeptide chain that consists of an amino acid sequence having at least 85% identity to the amino acid sequence represented by any one of SEQ ID NOs: 1 to 3 and further has immunoglobulin-binding activity. Examples of the furthermore preferable parent domain include a polypeptide chain consisting of an amino acid sequence represented by SEQ ID NO: 3, and a polypeptide chain that consists of an amino acid sequence having at least 85% identity to the amino acid sequence represented by SEQ ID NO: 3 and further has immunoglobulin-binding activity.

From the viewpoint of the increase in expression level in a transformant (PNAS, 1989, 86: 8247-8251, FIG. 2), or from the viewpoint of facilitating the preparation of a polynucleotide encoding an immunoglobulin-binding protein wherein multiple domains are linked (WO 2010/110288 A), the parent domain may contain substitution of Ala with Val at the position corresponding to position 1 of the amino acid sequence represented by SEQ ID NO: 3. Further, from the viewpoint that the chemical stability of an immunoglobulin-binding protein improves and the alkali resistance increases, the parent domain may further contain substitution of Gly with Ala at the position corresponding to position 29 of the amino acid sequence represented by SEQ ID NO: 3 (Non Patent Literature 1).

An immunoglobulin-binding domain mutant having a protein structure wherein the N-terminal region of a natural immunoglobulin-binding domain is deleted and the stability is higher than that of the natural immunoglobulin-binding domain has been reported (for example, WO 2013/109302 A, or WO 2017/194596 A) Accordingly, the parent domain may also be an immunoglobulin-binding domain mutant wherein amino acid residues corresponding to at least two residues (for example, two residues, four residues, six residues, or seven residues) from the N-terminus of an amino acid sequence represented by any one of SEQ ID NOs: 1 to 6 are deleted, as long as the domain has immunoglobulin-binding activity. Examples of the parent domain include polypeptide chains consisting of amino acid sequences represented by SEQ ID NOs: 57 to 62, respectively, and these polypeptide chains are mutant immunoglobulin-binding domains in each of which 2 to 7 residues from the N-terminus of the amino acid sequence represented by each of SEQ ID NOs: 1 to 6 are deleted.

Accordingly, the amino acid sequence having at least 85% identity to the amino acid sequence represented by any one of SEQ ID NOs: 1 to 6 of the above-described parent domains may be an amino acid sequence represented by any one of SEQ ID NOs: 57 to 62, or an amino acid sequence having at least 85% identity to the amino acid sequence represented by any one of SEQ ID NOs: 57 to 62. Further, the amino acid sequence having at least 85% identity to the amino acid sequence represented by any one of SEQ ID NOs: 1 to 6 may contain Val at a position corresponding to position 1 of the amino acid sequence represented by SEQ ID NO: 3, and/or may contain Ala at a position corresponding to position 29 of the amino acid sequence represented by SEQ ID NO: 3.

The mutant of the immunoglobulin-binding domain of the SpA can be prepared with the insertion, removal, substitution, or deletion of an amino acid residue or with the modification such as chemical modification of an amino acid residue, to an amino acid sequence of the immunoglobulin-binding domain of the SpA. As the means for the insertion, removal, substitution, or deletion of an amino acid residue, a known means such as site-specific mutation to a polynucleotide encoding the domain is included.

The mutant immunoglobulin-binding domain of the present invention is a polypeptide chain obtained by introducing at least one mutation into the above-described parent domain, the at least one mutation being selected from the group consisting of the following (a) to (f):

(a) substitution of an amino acid residue at at least one position selected from the group consisting of positions corresponding to positions 3, 6, and 11 of the amino acid sequence represented by SEQ ID NO: 3 with another amino acid residue, deletion of the amino acid residue at the at least one position, or insertion of another amino acid residue into a position in front of or behind the at least one position;

(b) substitution of an amino acid residue at at least one position selected from the group consisting of positions corresponding to positions 24 and 25 of the amino acid sequence represented by SEQ ID NO: 3 with another amino acid residue, deletion of the amino acid residue at the at least one position, or insertion of another amino acid residue into a position in front of or behind the at least one position;

(c) substitution of an amino acid residue at a position corresponding to position 39 of the amino acid sequence represented by SEQ ID NO: 3 with another amino acid residue, deletion of the amino acid residue at the position corresponding to position 39, or insertion of another amino acid residue into a position in front of or behind the position corresponding to position 39;

(d) substitution of an amino acid residue at a position corresponding to position 46 of the amino acid sequence represented by SEQ ID NO: 3 with another amino acid residue, deletion of the amino acid residue at the position corresponding to position 46, or insertion of another amino acid residue into a position in front of or behind the position corresponding to position 46;

(e) substitution of an amino acid residue at at least one position selected from the group consisting of positions corresponding to positions 4, 49, and 58 of the amino acid sequence represented by SEQ ID NO: 3 with another amino acid residue, deletion of the amino acid residue at the at least one position, or insertion of another amino acid residue into a position in front of or behind the at least one position; and (f) substitution of an amino acid residue at a position corresponding to position 23 of the amino acid sequence represented by SEQ ID NO: 3 with another amino acid residue, deletion of the amino acid residue at the position corresponding to position 23, or insertion of another amino acid residue into a position in front of or behind the position corresponding to position 23.

The mutation of (a) is substitution of an amino acid residue at at least one position selected from the group consisting of positions corresponding to positions 3, 6, and 11 of the amino acid sequence represented by SEQ ID NO: 3 with another amino acid residue, deletion of the amino acid residue at the at least one position, or insertion of another amino acid residue into a position in front of or behind the at least one position. The amino acid residues before the substitution at the positions corresponding to positions 3, 6, and 11 are each preferably Asn, and other amino acid residues to be replaced with these amino acid residues are preferably amino acid residues other than Ser, are each more preferably Ala, Arg, Asp, Cys, Gln, Glu, His, Ile, Leu, Lys, Met, Phe, Thr, Trp, Tyr, or Val, and furthermore preferably Gln. As the mutation of (a), single mutation of an amino acid residue at a position corresponding to position 3, 6, or 11 of the amino acid sequence represented by SEQ ID NO: 3 may be adopted, or multiple mutations wherein two or three of the amino acid residues at positions corresponding to positions 3, 6, and 11 are mutated may also be adopted. For example, as the mutation of (a), single substitution of an amino acid residue at the position corresponding to position 3, 6, or 11 of the amino acid sequence represented by SEQ ID NO: 3 may be adopted, or multiple substitutions wherein two or three of the amino acid residues at the positions corresponding to positions 3, 6 and 11 are replaced may also be adopted. Preferably, the mutation of (a) is ($a_1$) substitution of Asn with Gln at a position corresponding to position 3 of the amino acid sequence represented by SEQ ID NO: 3, ($a_2$) substitution of Asn with Ala at a position corresponding to position 3 of the amino acid sequence represented by SEQ ID NO: 3, ($a_3$) substitution of Asn with Asp at a position corresponding to position 3 of the amino acid sequence represented by SEQ ID NO: 3, ($a_4$) substitution of Asn with Gln at a position corresponding to position 6 of the amino acid sequence represented by SEQ ID NO: 3, ($a_5$) substitution of Asn with Ala at a position corresponding to position 6 of the amino acid sequence represented by SEQ ID NO: 3, ($a_6$) substitution of Asn with Asp at a position corresponding to position 6 of the amino acid sequence represented by SEQ ID NO: 3, ($a_7$) substitution of Asn with Gln at a position corresponding to position 11 of the amino acid sequence represented by SEQ ID NO: 3, ($a_8$) substitution of Asn with Ala at a position corresponding to position 11 of the amino acid sequence represented by SEQ ID NO: 3, ($a_9$) substitution of Asn with Arg at a position corresponding to position 11 of the amino acid sequence represented by SEQ ID NO: 3, ($a_{10}$) substitution of Asn with Asp at a position corresponding to position 11 of the amino acid sequence represented by SEQ ID NO: 3, ($a_{11}$) substitution of Asn with Cys at a position corresponding to position 11 of the amino acid sequence represented by SEQ ID NO: 3, ($a_{12}$) substitution of Asn with Glu at a position corresponding to position 11 of the amino acid sequence represented by SEQ ID NO: 3, ($a_{13}$) substitution of Asn with His at a position corresponding to position 11 of the amino acid sequence represented by SEQ ID NO: 3, ($a_{14}$) substitution of Asn with Ile at a position corresponding to position 11 of the amino acid sequence represented by SEQ ID NO: 3, ($a_{15}$) substitution of Asn with Leu at a position corresponding to position 11 of the amino acid sequence represented by SEQ ID NO: 3, ($a_{16}$) substitution of Asn with Lys at a position corresponding to position 11 of the amino acid sequence represented by SEQ ID NO: 3, ($a_{17}$) substitution of Asn with Met at a position corresponding to position 11 of the amino acid sequence represented by SEQ ID NO: 3, ($a_{18}$) substitution of Asn with Phe at a position corresponding to position 11 of the amino acid sequence represented by SEQ ID NO: 3, ($a_{19}$) substitution of Asn with Thr at a position corresponding to position 11 of the amino acid sequence represented by SEQ ID NO: 3, ($a_{20}$) substitution of Asn with Trp at a position corresponding to position 11 of the amino acid sequence represented by SEQ ID NO: 3, ($a_{21}$) substitution of Asn with Tyr at a position corresponding to position 11 of the amino acid sequence represented by SEQ ID NO: 3, ($a_{22}$) substitution of Asn with Val at a position corresponding to position 11 of the amino acid sequence represented by SEQ ID NO: 3, ($a_{23}$) substitution of Asns with Glns at positions corresponding to positions 3, 6, and 11 of the amino acid sequence represented by SEQ ID NO: 3, ($a_{24}$) substitution of Asn with Ala at a position corresponding to position 3 and substitution of Asn with Gln at a position corresponding to position 11, of the amino acid sequence represented by SEQ ID NO: 3, ($a_{25}$) substitution of Asn with Asp at a position corresponding to position 3 and substitution of Asn with Gln at a position corresponding to position 11, of the amino acid sequence represented by SEQ ID NO: 3, ($a_{26}$) substitution of Asn with Asp at a position corresponding to position 6 and substitution of Asn with Gln at a position corresponding to position 11, of the amino acid sequence represented by SEQ ID NO: 3, ($a_{27}$) substitution of Asn with Asp at a position corresponding to position 3, substitution of Asn with Asp at a position corresponding to position 6, and substitution of Asn with Gln at a position corresponding to position 11, of the amino acid sequence represented by SEQ ID NO: 3, or ($a_{28}$) substitution of Asn with Ala at a position corresponding to position 3, substitution of Asn with Asp at a position corresponding to position 6, and substitution of Asn with Gln at a position corresponding to position 11, of the amino acid sequence represented by SEQ ID NO: 3.

The mutation of (b) is substitution of an amino acid residue at at least one position selected from the group consisting of positions corresponding to positions 24 and 25 of the amino acid sequence represented by SEQ ID NO: 3 with another amino acid residue, deletion of the amino acid residue at the at least one position, or insertion of another amino acid residue into a position in front of or behind the at least one position. The amino acid residues before the substitution at the positions corresponding to positions 24 and 25 are each preferably Glu, and other amino acid residues to be replaced with these amino acid residues are each preferably Asp. As the mutation of (b), single mutation of an amino acid residue at a position corresponding to position 24 or 25 of the amino acid sequence represented by SEQ ID NO: 3 may be adopted, or multiple mutations wherein both of the amino acid residues at the positions corresponding to positions 24 and 25 are mutated may also be adopted. For example, as the mutation of (b), single substitution of an amino acid residue at a position corresponding to position 24 or 25 of the amino acid sequence represented by SEQ ID NO: 3 may be adopted, or multiple substitutions wherein both of the amino acid residues at positions corresponding to positions 24 and 25 are replaced may also be adopted. Preferably, the mutation of (b) is ($b_1$) substitution of Glu with Asp at a position corresponding to position 24 of the amino acid sequence represented by SEQ ID NO: 3, or ($b_2$) substitution of Glu with Asp at a position corresponding to position 25 of the amino acid sequence represented by SEQ ID NO: 3.

The mutation of (c) is substitution of an amino acid residue at a position corresponding to position 39 of the amino acid sequence represented by SEQ ID NO: 3 with another amino acid residue, deletion of the amino acid residue at the position corresponding to position 39, or insertion of another amino acid residue into a position in front of or behind the position corresponding to position 39. The amino acid residue before the substitution at the position corresponding to position 39 is preferably Ser, and the another amino acid residue to be replaced with the amino acid residue is preferably Lys or Arg. Preferably, the mutation of (c) is ($c_1$) substitution of Ser with Lys at a position corresponding to position 39 of the amino acid sequence represented by SEQ ID NO: 3, or (c) substitution of Ser with Arg at a position corresponding to position 39 of the amino acid sequence represented by SEQ ID NO: 3.

The mutation of (d) is substitution of an amino acid residue at a position corresponding to position 46 of the amino acid sequence represented by SEQ ID NO: 3 with another amino acid residue, deletion of the amino acid residue at the position corresponding to position 46, or insertion of another amino acid residue into a position in front of or behind the position corresponding to position 46. The amino acid residue before the substitution at the position corresponding to position 46 is preferably Ala, and the another amino acid residue to be replaced with the amino acid residue is preferably Asp, Glu, Lys, or Arg, and more preferably Asp, Glu, or Arg. Preferably, the mutation of (d) is ($d_1$) substitution of Ala with Asp at a position corresponding to position 46 of the amino acid sequence represented by SEQ ID NO: 3, ($d_2$) substitution of Ala with Glu at a position corresponding to position 46 of the amino acid sequence represented by SEQ ID NO: 3, ($d_3$) substitution of Ala with Lys at a position corresponding to position 46 of the amino acid sequence represented by SEQ ID NO: 3, or ($d_4$) substitution of Ala with Arg at a position corresponding to position 46 of the amino acid sequence represented by SEQ ID NO: 3.

The mutation of (e) is substitution of an amino acid residue at at least one position selected from the group consisting of positions corresponding to positions 4, 49, and 58 of the amino acid sequence represented by SEQ ID NO: 3 with another amino acid residue, deletion of the amino acid residue at the at least one position, or insertion of another amino acid residue into a position in front of or behind the at least one position. The deleted amino acid residues at the positions corresponding to positions 4, 49, and 58 are each preferably Lys. In the positions corresponding to positions 4, 49, and 58, the amino acid residues before the substitution are each preferably Lys, and other amino acid residues to be replaced with these amino acid residues are each preferably Arg. As the mutation of (e), single mutation of an amino acid residue at a position corresponding to position 4, 49, or 58 of the amino acid sequence represented by SEQ ID NO: 3 may be adopted, or multiple mutations wherein two or three of the amino acid residues at the positions corresponding to positions 4, 49, and 58 are mutated may also be adopted. For example, as the mutation of (e), deletion or substitution of an amino acid residue alone at a position corresponding to position 4, 49, or 58 of the amino acid sequence represented by SEQ ID NO: 3 may be adopted, or multiple mutations wherein two or three of the amino acid residues at the positions corresponding to positions 4, 49, and 58 are deleted or replaced may also be adopted. Preferably, the mutation of (e) is ($e_1$) deletion of Lys at a position corresponding to position 4 of the amino acid sequence represented by SEQ ID NO: 3, ($e_2$) substitution of Lys with Arg at a position corresponding to position 49 of the amino acid sequence represented by SEQ ID NO: 3, ($e_3$) deletion of Lys at a position corresponding to position 58 of the amino acid sequence represented by SEQ ID NO: 3, or ($e_4$) substitution of Lys with Arg at a position corresponding to position 58 of the amino acid sequence represented by SEQ ID NO: 3.

The mutation of (f) is substitution of an amino acid residue at a position corresponding to position 23 of the amino acid sequence represented by SEQ ID NO: 3 with another amino acid residue, deletion of the amino acid residue at the position corresponding to position 23, or insertion of another amino acid residue into a position in front of or behind the position corresponding to position 23. The amino acid residue before the substitution at the position corresponding to position 23 is preferably Thr, and the another amino acid residue to be replaced with the amino acid residue is preferably Arg, Leu, or Ser. Preferably, the mutation of (f) is ($f_1$) substitution of Thr with Arg at a position corresponding to position 23 of the amino acid sequence represented by SEQ ID NO: 3, ($f_2$) substitution of Thr with Leu at a position corresponding to position 23 of the amino acid sequence represented by SEQ ID NO: 3, or ($f_3$) substitution of Thr with Ser at a position corresponding to position 23 of the amino acid sequence represented by SEQ ID NO: 3.

In a preferable embodiment, the mutant immunoglobulin-binding domain of the present invention is produced by introducing at least one mutation selected from the group consisting of the (a) to (f) into a polypeptide chain consisting of an amino acid sequence represented by any one of SEQ ID NOs: 1 to 6. In another preferable embodiment, the mutant immunoglobulin-binding domain of the present invention is produced by introducing at least one mutation selected from the group consisting of the (a) to (f) into a polypeptide chain consisting of an amino acid sequence having at least 85% identity to an amino acid sequence represented by any one of SEQ ID NOs: 1 to 6 and further having immunoglobulin-binding activity.

In a more preferable embodiment, the mutant immunoglobulin-binding domain of the present invention is produced by introducing at least one mutation selected from the group consisting of the (a) to (f) into a polypeptide chain consisting of an amino acid sequence represented by any one of SEQ ID NOs: 1 to 3.

In another more preferable embodiment, the mutant immunoglobulin-binding domain of the present invention is produced by introducing at least one mutation selected from the group consisting of the (a) to (f) into a polypeptide chain consisting of an amino acid sequence having at least 85% identity to an amino acid sequence represented by any one of SEQ ID NOs: 1 to 3 and further having immunoglobulin-binding activity.

In a furthermore preferable embodiment, the mutant immunoglobulin-binding domain of the present invention is produced by introducing at least one mutation selected from the group consisting of the (a) to (f) into a polypeptide chain consisting of an amino acid sequence represented by SEQ ID NO: 3, or a polypeptide chain consisting of an amino acid sequence having at least 85% identity to the amino acid sequence represented by SEQ ID NO: 3 and further having immunoglobulin-binding activity.

The mutation to be introduced may be any one of the (a) to (f), or a combination of two or more of the (a) to (f) (that is, mutation of amino acid residues at positions corresponding to at least two of positions 3, 6, 11, 24, 25, 39, 46, 4, 49, 58, and 23 of the amino acid sequence represented by SEQ ID NO: 3), and is preferably at least one mutation selected from the group consisting of the above ($a_1$), ($a_2$), ($a_3$), ($a_4$), ($a_5$), ($a_6$), ($a_7$), ($a_8$), ($a_9$), ($a_{10}$), ($a_{11}$), ($a_{12}$), ($a_{13}$), ($a_{14}$), ($a_{15}$), ($a_{16}$), ($a_{17}$), ($a_{18}$), ($a_{19}$), ($a_{20}$), ($a_{21}$), ($a_{22}$), ($b_1$), ($b_2$), ($c_1$), ($c_2$), ($d_1$), ($d_2$), ($d_3$), ($d_4$), ($e_1$), ($e_2$), ($e_3$), ($e_4$), ($f_1$), ($f_2$), and ($f_3$), or a combination of two or more mutations thereof. Examples of the combination of two or more mutations include the above ($a_{23}$) to ($a_{28}$). Other examples of the combination of two or more mutations include a combination of any one of the above ($a_1$) to ($a_{28}$) and any one or more of the above ($b_1$) to ($f_3$), preferably a combination of any one of the above ($a_1$) to ($a_{22}$) and any one or more of the above ($e_1$) to ($f_3$), more preferably a combination of any one of the above ($a_7$) to ($a_{22}$) and any one or more of the above ($e_2$), ($e_4$), ($f_1$), ($f_2$), and ($f_3$), furthermore preferably a combination of ($a_7$) and any one or more of the above ($e_2$), ($e_4$), ($f_1$), ($f_2$), and ($f_3$), and still furthermore preferably the following combinations of:
  ($g_1$) a combination of the above ($a_7$) and ($f_1$);
  ($g_2$) a combination of the above ($a_7$) and ($f_2$);
  ($g_3$) a combination of the above ($a_7$) and ($f_3$);
  ($g_4$) a combination of the above ($a_7$) and ($e_2$);
  ($g_5$) a combination of the above ($a_7$) and ($e_4$);
  ($g_6$) a combination of the above ($a_7$), ($f_1$), and ($e_2$);
  ($g_7$) a combination of the above ($a_7$), ($f_2$), and ($e_2$); and
  ($g_8$) a combination of the above ($a_7$), ($f_3$), and ($e_2$).

In a preferable embodiment, the at least one mutation selected from the group consisting of the (a) to (f) is the above ($a_1$), ($a_2$), ($a_3$), ($a_4$), ($a_5$), ($a_6$), ($a_7$), ($a_8$), ($a_9$), ($a_{10}$), ($a_{11}$), ($a_{12}$), ($a_{13}$), ($a_{14}$), ($a_{15}$), ($a_{16}$), ($a_{17}$), ($a_{18}$), ($a_{19}$), ($a_{20}$), ($a_{21}$), ($a_{22}$), ($a_{23}$), ($a_{24}$), ($a_{25}$), ($a_{26}$), ($a_{27}$), ($a_{28}$), ($b_1$), ($b_2$), ($c_1$), ($c_2$), ($d_1$), ($d_2$), ($d_3$), ($d_4$), ($e_1$), ($e_2$), ($e_3$), ($e_4$), ($f_1$), ($f_2$), ($f_3$), ($g_1$), ($g_2$), ($g_3$), ($g_4$), ($g_5$), ($g_6$), ($g_7$), or ($g_8$). In another one example, the at least one mutation selected from the group consisting of the (a) to (f) includes any one of the mutations of the ($a_1$) to ($g_8$), but does not include any mutation in the mutations of the ($a_1$) to ($g_8$), other than the above one. Further, in another one example, the at least one mutation selected from the group consisting of the (a) to (f) may not include a case of only single mutation of the ($e_2$), ($e_3$), or ($e_4$) or a case of only double mutation of ($e_2$) and ($e_3$) or ($e_2$) and ($e_4$).

An example of the means for mutating the parent domain includes a method for introducing mutation to a polynucleotide encoding the parent domain so that, for example, substitution, deletion, or insertion of a desired amino acid residue is generated. Examples of the specific technique for mutation introduction to a polynucleotide include site-specific mutation, a homologous recombination method, and a SOE (splicing by overlap extension)-PCR method (Gene, 1989, 77: 61-68). The detailed procedures of such techniques are well known to a person skilled in the art.

The produced mutant immunoglobulin-binding domain of the present invention has immunoglobulin-binding activity, and functions as an immunoglobulin-binding domain. Further, the mutant immunoglobulin-binding domain of the present invention has improved alkali resistance as compared with that of the domain before mutation (parent domain). Accordingly, the mutant immunoglobulin-binding domain of the present invention can be used suitably as an affinity ligand.

A preferable example of the mutant immunoglobulin-binding domain of the present invention obtained by the above procedure includes a polypeptide chain consisting of an amino acid sequence that has at least 85% identity to an amino acid sequence represented by any one of SEQ ID NOs: 1 to 6 and further has at least one mutation selected from the group consisting of the above (a) to (f), and having immunoglobulin-binding activity.

A more preferable example of the mutant immunoglobulin-binding domain of the present invention includes a polypeptide chain consisting of an amino acid sequence that has at least 85% identity to an amino acid sequence represented by any one of SEQ ID NOs: 1 to 3 and further has at least one mutation selected from the group consisting of the above (a) to (f), and having immunoglobulin-binding activity.

A furthermore preferable example of the mutant immunoglobulin-binding domain of the present invention includes a polypeptide chain consisting of an amino acid sequence that has at least 85% identity to an amino acid sequence represented by SEQ ID NO: 3 and has at least one mutation selected from the group consisting of the above (a) to (f), and having immunoglobulin-binding activity.

The at least one mutation selected from the group consisting of the (a) to (f) is preferably at least one selected from the group consisting of the above ($a_1$), ($a_2$), ($a_3$), ($a_4$), ($a_5$), ($a_6$), ($a_7$), ($a_8$), ($a_9$), ($a_{10}$), ($a_{11}$), ($a_{12}$), ($a_{13}$), ($a_{14}$), ($a_{15}$), ($a_{16}$), ($a_{17}$), ($a_{18}$), ($a_{19}$), ($a_{20}$), ($a_{21}$), ($a_{22}$), ($b_1$), ($b_2$), ($c_1$), ($c_2$), ($d_1$), ($d_2$), ($d_3$), ($d_4$), ($e_1$), ($e_2$), ($e_3$), ($e_4$), ($f_1$), ($f_2$), and ($f_3$), and more preferably the above ($a_1$), ($a_2$), ($a_3$), ($a_4$), ($a_5$), ($a_6$), ($a_7$), ($a_8$), ($a_9$), ($a_{10}$), ($a_{11}$), ($a_{12}$), ($a_{13}$), ($a_{14}$), ($a_{15}$), ($a_{16}$), ($a_{17}$), ($a_{18}$), ($a_{19}$), ($a_{20}$), ($a_{21}$), ($a_{22}$), ($a_{23}$), ($a_{24}$), ($a_{25}$), ($a_{26}$), ($a_{27}$), ($a_{28}$), ($b_1$), ($b_2$), ($c_1$), ($c_2$), ($d_1$), ($d_2$), ($d_3$), ($d_4$), ($e_1$), ($e_2$), ($e_3$), ($e_4$), ($f_1$), ($f_2$), ($f_3$), ($g_1$), ($g_2$), ($g_3$), ($g_4$), ($g_5$), ($g_6$), ($g_7$), or ($g_8$). In another one example, the at least one mutation selected from the group consisting of the (a) to (f) includes any one of the mutations of the ($a_1$) to ($g_8$), but does not include any mutation in the mutations of the ($a_1$) to ($g_8$), other than the above one. Further, in another one example, the at least one mutation selected from the group consisting of the (a) to (f) may not include a case of only single mutation of the ($e_2$), ($e_3$), or ($e_4$), or a case of only double mutation of ($e_2$) and ($e_3$) or ($e_2$) and ($e_4$).

Alternatively, a preferable example of the mutant immunoglobulin-binding domain of the present invention includes a polypeptide chain consisting of an amino acid sequence that has at least 85% identity to an amino acid sequence represented by any one of SEQ ID NOs: 1 to 6 and further has at least one amino acid residue selected from the group consisting of the following ($A_1$) to ($F_3$):
  ($A_1$) Gln at a position corresponding to position 3 of the amino acid sequence represented by SEQ ID NO: 3;
  ($A_2$) Ala at a position corresponding to position 3 of the amino acid sequence represented by SEQ ID NO: 3;
  ($A_3$) Asp at a position corresponding to position 3 of the amino acid sequence represented by SEQ ID NO: 3;

($A_4$) Gln at a position corresponding to position 6 of the amino acid sequence represented by SEQ ID NO: 3;
($A_5$) Ala at a position corresponding to position 6 of the amino acid sequence represented by SEQ ID NO: 3;
($A_6$) Asp at a position corresponding to position 6 of the amino acid sequence represented by SEQ ID NO: 3;
($A_7$) Gln at a position corresponding to position 11 of the amino acid sequence represented by SEQ ID NO: 3;
($A_8$) Ala at a position corresponding to position 11 of the amino acid sequence represented by SEQ ID NO: 3;
($A_9$) Arg at a position corresponding to position 11 of the amino acid sequence represented by SEQ ID NO: 3;
($A_{10}$) Asp at a position corresponding to position 11 of the amino acid sequence represented by SEQ ID NO: 3;
($A_{11}$) Cys at a position corresponding to position 11 of the amino acid sequence represented by SEQ ID NO: 3;
($A_{12}$) Glu at a position corresponding to position 11 of the amino acid sequence represented by SEQ ID NO: 3;
($A_{13}$) His at a position corresponding to position 11 of the amino acid sequence represented by SEQ ID NO: 3;
($A_{14}$) Ile at a position corresponding to position 11 of the amino acid sequence represented by SEQ ID NO: 3;
($A_{15}$) Leu at a position corresponding to position 11 of the amino acid sequence represented by SEQ ID NO: 3;
($A_{16}$) Lys at a position corresponding to position 11 of the amino acid sequence represented by SEQ ID NO: 3;
($A_{17}$) Met at a position corresponding to position 11 of the amino acid sequence represented by SEQ ID NO: 3;
($A_{18}$) Phe at a position corresponding to position 11 of the amino acid sequence represented by SEQ ID NO: 3;
($A_{19}$) Thr at a position corresponding to position 11 of the amino acid sequence represented by SEQ ID NO: 3;
($A_{20}$) Trp at a position corresponding to position 11 of the amino acid sequence represented by SEQ ID NO: 3;
($A_{21}$) Tyr at a position corresponding to position 11 of the amino acid sequence represented by SEQ ID NO: 3;
($A_{22}$) Val at a position corresponding to position 11 of the amino acid sequence represented by SEQ ID NO: 3;
($B_1$) Asp at a position corresponding to position 24 of the amino acid sequence represented by SEQ ID NO: 3;
($B_2$) Asp at a position corresponding to position 25 of the amino acid sequence represented by SEQ ID NO: 3;
($C_1$) Lys at a position corresponding to position 39 of the amino acid sequence represented by SEQ ID NO: 3;
($C_2$) Arg at a position corresponding to position 39 of the amino acid sequence represented by SEQ ID NO: 3;
($D_1$) Asp at a position corresponding to position 46 of the amino acid sequence represented by SEQ ID NO: 3;
($D_2$) Glu at a position corresponding to position 46 of the amino acid sequence represented by SEQ ID NO: 3;
($D_3$) Lys at a position corresponding to position 46 of the amino acid sequence represented by SEQ ID NO: 3;
($D_4$) Arg at a position corresponding to position 46 of the amino acid sequence represented by SEQ ID NO: 3;
($E_1$) deletion of Lys at a position corresponding to position 4 of the amino acid sequence represented by SEQ ID NO: 3,
(E2) Arg at a position corresponding to position 49 of the amino acid sequence represented by SEQ ID NO: 3;
($E_3$) deletion of Lys at a position corresponding to position 58 of the amino acid sequence represented by SEQ ID NO: 3,
($E_4$) Arg at a position corresponding to position 58 of the amino acid sequence represented by SEQ ID NO: 3;
($F_1$) Arg at a position corresponding to position 23 of the amino acid sequence represented by SEQ ID NO: 3;
(F2) Leu at a position corresponding to position 23 of the amino acid sequence represented by SEQ ID NO: 3; and
($F_3$) Ser at a position corresponding to position 23 of the amino acid sequence represented by SEQ ID NO: 3, or of an amino acid sequence that has a combination of two or more amino acid residues of the above ($A_1$) to ($F_3$). The amino acid sequence that has at least 85% identity to the amino acid sequence represented by any one of SEQ ID NOs: 1 to 6 is preferably an amino acid sequence having at least 85% identity to the amino acid sequence represented by any one of SEQ ID NOs: 1 to 3, and more preferably an amino acid sequence having at least 85% identity to the amino acid sequence represented by SEQ ID NO 3.

Examples of the combination of two or more amino acid residues include the following ($A_{23}$) to ($A_{28}$):
($A_{23}$) Glns at positions corresponding to positions 3, 6, and 11 of the amino acid sequence represented by SEQ ID NO: 3;
($A_{24}$) Ala at a position corresponding to position 3, Asp at a position corresponding to position 6, and Gln at a position corresponding to position 11, of the amino acid sequence represented by SEQ ID NO: 3;
($A_{25}$) Asp at a position corresponding to position 3, and Gln at a position corresponding to position 11, of the amino acid sequence represented by SEQ ID NO: 3;
($A_{26}$) Asp at a position corresponding to position 6, and Gln at a position corresponding to position 11, of the amino acid sequence represented by SEQ ID NO: 3;
($A_{27}$) Asp at a position corresponding to position 3, Asp at a position corresponding to position 6, and Gln at a position corresponding to position 11, of the amino acid sequence represented by SEQ ID NO: 3; and
($A_{28}$) Ala at a position corresponding to position 3, Asp at a position corresponding to position 6, and Gln at a position corresponding to position 11, of the amino acid sequence represented by SEQ ID NO: 3.

Another example of the combination of two or more amino acid residues includes a combination of any one of the above ($A_1$) to ($A_{20}$) and any one or more of the above ($B_1$) to ($F_3$), preferably includes a combination of any one of the above ($A_1$) to ($A_{22}$) and any one or more of the above ($E_1$) to ($F_3$), more preferably includes a combination of any one of the above ($A_7$) to ($A_{22}$) and any one or more of the above ($E_2$), ($E_4$), ($F_1$), ($F_2$), and ($F_3$), furthermore preferably includes a combination of the above (A) and any one or more of the above ($E_2$), ($E_4$), ($F_1$), ($F_2$), and ($F_3$), and still furthermore preferably includes the following combination of:
(G1) the above ($A_7$) and ($F_1$);
(G2) the above ($A_7$) and ($F_2$);
($G_3$) the above ($A_7$) and ($F_3$);
($G_4$) the above ($A_1$) and ($E_2$);
($G_5$) the above ($A_7$) and ($E_4$);
($G_6$) the above ($A_7$), ($F_1$), and ($E_2$);
(G7) the above ($A_7$), ($F_2$), and ($E_2$); or
($G_8$) the above ($A_7$), ($F_3$), and ($E_2$).

Alternatively, a more preferable example of the mutant immunoglobulin-binding domain of the present invention includes a polypeptide chain consisting of an amino acid sequence having at least 85% identity to an amino acid sequence represented by any one of SEQ ID NOs: 1 to 6 and further containing the following:

($A_1$) Gln at a position corresponding to position 3 of the amino acid sequence represented by SEQ ID NO: 3;
($A_2$) Ala at a position corresponding to position 3 of the amino acid sequence represented by SEQ ID NO: 3;
($A_3$) Asp at a position corresponding to position 3 of the amino acid sequence represented by SEQ ID NO: 3;
($A_4$) Gln at a position corresponding to position 6 of the amino acid sequence represented by SEQ ID NO: 3;
($A_5$) Ala at a position corresponding to position 6 of the amino acid sequence represented by SEQ ID NO: 3;
($A_6$) Asp at a position corresponding to position 6 of the amino acid sequence represented by SEQ ID NO: 3;
($A_7$) Gln at a position corresponding to position 11 of the amino acid sequence represented by SEQ ID NO: 3;
($A_8$) Ala at a position corresponding to position 11 of the amino acid sequence represented by SEQ ID NO: 3;
($A_9$) Arg at a position corresponding to position 11 of the amino acid sequence represented by SEQ ID NO: 3;
($A_{10}$) Asp at a position corresponding to position 11 of the amino acid sequence represented by SEQ ID NO: 3;
($A_{11}$) Cys at a position corresponding to position 11 of the amino acid sequence represented by SEQ ID NO: 3;
($A_{12}$) Glu at a position corresponding to position 11 of the amino acid sequence represented by SEQ ID NO: 3;
($A_{13}$) His at a position corresponding to position 11 of the amino acid sequence represented by SEQ ID NO: 3;
($A_{14}$) Ile at a position corresponding to position 11 of the amino acid sequence represented by SEQ ID NO: 3;
($A_{15}$) Leu at a position corresponding to position 11 of the amino acid sequence represented by SEQ ID NO: 3;
($A_{16}$) Lys at a position corresponding to position 11 of the amino acid sequence represented by SEQ ID NO: 3;
($A_{17}$) Met at a position corresponding to position 11 of the amino acid sequence represented by SEQ ID NO: 3;
($A_{18}$) Phe at a position corresponding to position 11 of the amino acid sequence represented by SEQ ID NO: 3;
($A_{19}$) Thr at a position corresponding to position 11 of the amino acid sequence represented by SEQ ID NO: 3;
($A_{20}$) Trp at a position corresponding to position 11 of the amino acid sequence represented by SEQ ID NO: 3;
($A_{21}$) Tyr at a position corresponding to position 11 of the amino acid sequence represented by SEQ ID NO: 3;
($A_{22}$) Val at a position corresponding to position 11 of the amino acid sequence represented by SEQ ID NO: 3;
($A_{23}$) Glns at positions corresponding to positions 3, 6, and 11 of the amino acid sequence represented by SEQ ID NO: 3;
($A_{24}$) Ala at a position corresponding to position 3, and Gln at a position corresponding to position 11, of the amino acid sequence represented by SEQ ID NO: 3;
($A_{25}$) Asp at a position corresponding to position 3, and Gln at a position corresponding to position 11, of the amino acid sequence represented by SEQ ID NO: 3;
($A_{26}$) Asp at a position corresponding to position 6, and Gln at a position corresponding to position 11, of the amino acid sequence represented by SEQ ID NO: 3;
($A_{27}$) Asp at a position corresponding to position 3, Asp at a position corresponding to position 6, and Gln at a position corresponding to position 11, of the amino acid sequence represented by SEQ ID NO: 3;
($A_{28}$) Ala at a position corresponding to position 3, Asp at a position corresponding to position 6, and Gln at a position corresponding to position 11, of the amino acid sequence represented by SEQ ID NO: 3;
($B_1$) Asp at a position corresponding to position 24 of the amino acid sequence represented by SEQ ID NO: 3;
($B_2$) Asp at a position corresponding to position 25 of the amino acid sequence represented by SEQ ID NO: 3;
($C_1$) Lys at a position corresponding to position 39 of the amino acid sequence represented by SEQ ID NO: 3;
($C_2$) Arg at a position corresponding to position 39 of the amino acid sequence represented by SEQ ID NO: 3;
($D_1$) Asp at a position corresponding to position 46 of the amino acid sequence represented by SEQ ID NO: 3;
($D_2$) Glu at a position corresponding to position 46 of the amino acid sequence represented by SEQ ID NO: 3;
($D_3$) Lys at a position corresponding to position 46 of the amino acid sequence represented by SEQ ID NO: 3;
($D_4$) Arg at a position corresponding to position 46 of the amino acid sequence represented by SEQ ID NO: 3;
($E_1$) deletion of Lys at a position corresponding to position 4 of the amino acid sequence represented by SEQ ID NO: 3,
($E_2$) Arg at a position corresponding to position 49 of the amino acid sequence represented by SEQ ID NO: 3;
($E_3$) deletion of Lys at a position corresponding to position 58 of the amino acid sequence represented by SEQ ID NO: 3,
($E_4$) Arg at a position corresponding to position 58 of the amino acid sequence represented by SEQ ID NO: 3;
($F_1$) Arg at a position corresponding to position 23 of the amino acid sequence represented by SEQ ID NO: 3;
($F_2$) Leu at a position corresponding to position 23 of the amino acid sequence represented by SEQ ID NO: 3;
($F_3$) Ser at a position corresponding to position 23 of the amino acid sequence represented by SEQ ID NO: 3;
($G_1$) the above ($A_7$) and ($F_1$);
($G_2$) the above ($A_1$) and ($F_2$);
($G_3$) the above ($A_7$) and ($F_3$);
($G_4$) the above ($A_7$) and ($E_2$);
($G_5$) the above ($A_7$) and ($E_4$);
($G_6$) the above ($A_7$), ($F_1$), and ($E_2$);
($G_7$) the above ($A_7$), ($F_2$) and ($E_2$); or
($G_8$) the above ($A_7$), ($F_3$) and ($E_2$).

The amino acid sequence having at least 85% identity to the amino acid sequence represented by any one of SEQ ID NOs: 1 to 6 is preferably an amino acid sequence having at least 85% identity to the amino acid sequence represented by any one of SEQ ID NOs: 1 to 3, and more preferably an amino acid sequence having at least 85% identity to the amino acid sequence represented by SEQ ID NO 3. In another one example, the mutant immunoglobulin-binding domain of the present invention contains any one of the amino acid residues of the above ($A_1$) to ($G_8$) or the deletions of the ($A_1$) to ($G_8$), but does not contain any amino acid residue of the ($A_1$) to ($G_8$) or any deletion of the ($A_1$) to ($G_8$), other than the above one. Further, in another one example, at least one amino acid residue selected from the group consisting of ($A_1$) to ($F_3$) of the mutant immunoglobulin-binding domain of the present invention or the deletion of the at least one amino acid residue may not contain single mutation of ($E_2$) K49R, ($E_3$) ΔK58, or ($E_4$) K58R or double mutation of K49RΔK58 or K49RK58R.

In the mutant immunoglobulin-binding domain of the present invention, the amino acid sequence having at least 85% identity to the amino acid sequence represented by any one of SEQ ID NOs: 1 to 6 may be an amino acid sequence having at least 85% identity to an amino acid sequence represented by any one of SEQ ID NOs: 57 to 62. Further, in the mutant immunoglobulin-binding domain of the present invention, the amino acid sequence having at least 85% identity to the amino acid sequence represented by any one of SEQ ID NOs: 1 to 3 may be an amino acid sequence having at least 85% identity to an amino acid sequence represented by any one of SEQ ID NOs: 57 to 59. However, the mutant immunoglobulin-binding domain of the present invention consisting of an amino acid sequence having at least 85% identity to the amino acid sequence represented by any one of SEQ ID NOs: 57 to 62 may not contain any mutations of amino acid residues at positions corresponding to positions 3 and 4 of the amino acid sequence represented by SEQ ID NO: 3 of the above-described mutations of (a) to (f).

Preferably, the mutant immunoglobulin-binding domain of the present invention contains Val at a position corresponding to position 1 of the amino acid sequence represented by SEQ ID NO: 3, and/or contains Ala at a position corresponding to position 29 of the amino acid sequence represented by SEQ ID NO: 3.

A furthermore preferable example of the mutant immunoglobulin-binding domain of the present invention includes a polypeptide chain consisting of an amino acid sequence represented by any one of SEQ ID NOs: 7 to 53.

The immunoglobulin-binding protein according to the present invention may contain one or more of the above-described mutant immunoglobulin-binding domains of the present invention. Preferably, the immunoglobulin-binding protein according to the present invention contains two or more, more preferably three or more, furthermore preferably four or more, still furthermore preferably five or more, and even still more preferably six or more of the mutant immunoglobulin-binding domains of the present invention. On the other hand, the immunoglobulin-binding protein according to the present invention contains preferably 12 or less, more preferably 8 or less, and furthermore preferably 7 or less of the mutant immunoglobulin-binding domains of the present invention. For example, the immunoglobulin-binding protein according to the present invention contains preferably 2 to 12, more preferably 3 to 8, and furthermore preferably 4 to 7 of the mutant immunoglobulin-binding domains of the present invention. In a case where the immunoglobulin-binding protein according to the present invention contains two or more of the mutant immunoglobulin-binding domains of the present invention, these mutant immunoglobulin-binding domains may be the same as or different from each other, but are preferably the same as each other.

The immunoglobulin-binding protein according to the present invention may contain some immunoglobulin-binding domains other than the above-described mutant immunoglobulin-binding domains of the present invention. Examples of the domains other than the above-described mutant immunoglobulin-binding domains include a natural-form SpA immunoglobulin-binding domain (for example, a B domain, Z domain, C domain, or D domain of SpA), or a mutant of the natural-form SpA immunoglobulin-binding domain other than the mutant immunoglobulin-binding domains of the present invention.

A preferable example of the immunoglobulin-binding protein according to the present invention includes a polypeptide wherein amino acid sequences of two or more of the mutant immunoglobulin-binding domains of the present invention are linearly linked. The number of the mutant immunoglobulin-binding domains contained in the immunoglobulin-binding protein according to the present invention is preferably 2 to 12 domains, more preferably 3 to 8 domains, and furthermore preferably 4 to 7 domains. A more preferable example of the immunoglobulin-binding protein according to the present invention includes a polypeptide consisting of an amino acid sequence wherein two or more amino acid sequences selected from the amino acid sequences represented by SEQ ID NOs: 7 to 53 are linearly linked. A furthermore preferable example of the immunoglobulin-binding protein according to the present invention includes a polypeptide consisting of an amino acid sequence wherein 2 to 12 amino acid sequences, more preferably 3 to 8 amino acid sequences, and furthermore preferably 4 to 7 amino acid sequences, selected from the amino acid sequences represented by SEQ ID NOs: 7 to 53, are linearly linked. A still furthermore preferable example of the immunoglobulin-binding protein according to the present invention includes a polypeptide consisting of an amino acid sequence wherein 2 to 12 amino acid sequences, more preferably 3 to 8 amino acid sequences, and furthermore preferably 4 to 7 amino acid sequences, selected from the amino acid sequences represented by SEQ ID NOs: 7 to 53, are linearly linked. However, preferable examples of the protein of the present invention are not limited to the above proteins. In this regard, in the present invention, the expression that amino acid sequences are "linearly linked" means a structure wherein two or more amino acid sequences are linked in series with or without a linker. For example, in a case of with a linker, the expression "linearly linked" means a structure wherein the C-terminus of one amino acid sequence and the N-terminus of another amino acid sequence are linked in series with a linker, and on the other hand, in a case of without a linker, the expression "linearly linked" means a structure wherein the C-terminus of one amino acid sequence and the N-terminus of another amino acid sequence are linked in series by a peptide bond.

From the viewpoint of, for example, the increase in the amount of the immunoglobulin-binding protein according to the present invention immobilized on a carrier, the increase in the number of binding points to a carrier, or the increase in the antibody binding capacity, any amino acid residue or peptide may be added or inserted at any one or more of the N-terminus, the C-terminus, of the immunoglobulin-binding domain contained in the immunoglobulin-binding protein according to the present invention, and between domains. Preferable examples of the amino acid residue or peptide to be added or inserted include Cys, Lys, Pro, (Pro)m, (Ala-Pro)n, and (Glu-Ala-Ala-Ala-Lys)p (m represents an integer of 2 to 300 and preferably 12 to 24, n represents an integer of 4 or more and preferably 4 to 10, and p represents an integer of 2 or more and preferably 2 to 6).

2. Production of Immunoglobulin-Binding Protein

The immunoglobulin-binding protein according to the present invention can be produced by, for example, a known technique in the field, such as a chemical synthesis method based on the amino acid sequence, or a recombinant method. For example, the immunoglobulin-binding protein according to the present invention can be produced by utilizing a known gene recombination technique disclosed in, for example, Current Protocols In Molecular Biology by Frederick M. Ausbel, et al., or Molecular Cloning (Cold Spring Harbor Laboratory Press, 3rd edition, 2001) edited by Sambrook, et al. That is, an expression vector containing a polynucleotide encoding the immunoglobulin-binding protein according to the present invention is transformed into a host such as *E. coli*, the obtained recombinant is cultured in an appropriate liquid medium, and from the cells after the culture, the desired protein can be obtained in a large amount and economically. As a preferable expression vector, any known vector that is replicable in a host cell can be used, and examples of the vector include a plasmid disclosed in the specification of U.S. Pat. No. 5,151,350, and a plasmid disclosed in, for example, Molecular Cloning (Cold Spring Harbor Laboratory Press, 3rd edition, 2001) edited by Sambrook, et al. Further, as the host for transformation, it is not particularly limited, and a known host used to express a recombinant protein of, for example, a bacterium such as *E. coli*, a fungus, an insect cell, or a mammalian cell can be used. In order to transform a host by introducing a nucleic acid into the host, any method known in the technical field may be used depending on the host, and for example, a known method disclosed in Molecular Cloning (Cold Spring Harbor Laboratory Press, 3rd edition, 2001) edited by Sambrook, et al., or the like can be utilized. The method for recovering the protein expressed by culturing the obtained transformant (preferably cells such as bacteria) is well known to a person skilled in the art. Alternatively, the immunoglobulin-binding protein according to the present invention may be expressed by using a cell-free protein synthesis system.

Accordingly, the present invention is also to provide a polynucleotide (for example, DNA) encoding the immunoglobulin-binding protein according to the present invention, a vector containing the polynucleotide, and a transformant containing the vector.

3. Affinity Carrier

The immunoglobulin-binding protein according to the present invention can be used as an affinity ligand. With the immobilization of the immunoglobulin-binding protein according to the present invention on a solid carrier, an affinity carrier having the immunoglobulin-binding protein according to the present invention as a ligand can be produced. The affinity carrier is a carrier having the immunoglobulin-binding protein according to the present invention as a ligand, and has an immunoglobulin-binding activity. Further, the affinity carrier has improved alkali resistance as compared with that of a carrier having wild-type Protein A or a domain of the wild-type Protein A as a ligand.

The form of the solid carrier contained in the affinity carrier according to the present invention can be any form such as particles, a membrane, a plate, a tube, a needle, or fibers. The carrier may be porous or non-porous. These carriers can be used as packed beds, or can also be used in suspension form. Those known as an expanded bed and a pure suspended solid are included in the suspension form, and particles can be free to move in the suspension form. In a case of a monolith, a packed bed, or an expanded bed, the separation procedure is generally performed in accordance with a conventional chromatography by a concentration gradient. In a case of a pure suspended solid, a batch method is used. Preferably, the carrier is a filler. Alternatively, the carrier may also be in a form of a chip, a capillary, or even a filter.

In one embodiment, the solid carrier in a case of being in a form of particles has a particle diameter of preferably 20 µm or more and 200 µm or less. For example, in a case where the carrier is a synthetic polymer, the particle diameter is preferably 20 µm or more and more preferably 30 µm or more, and preferably 100 µm or less and more preferably 80 µm or less, and is, for example, preferably 20 to 100 µm and more preferably 30 to 80 µm. For example, in a case where the carrier is a polysaccharide, the particle diameter is preferably 50 µm or more and more preferably 60 µm or more, and preferably 200 µm or less and more preferably 150 µm or less, and is, for example, preferably 50 to 200 µm and more preferably 60 to 150 µm. When the particle diameter is less than 20 µm, the column pressure becomes high under a high flow rate, and the particles cannot withstand practical use. When the particle diameter exceeds 200 µm, the amount (binding capacity) of immunoglobulin that binds to an affinity carrier may become less amount in some cases. In this regard, the expression "particle diameter" in the present specification means a volume average particle diameter as measured by a laser diffraction method in accordance with ISO 13320 and JIS Z 8825-1. Specifically, the particle diameter means an average particle diameter obtained by measuring a particle diameter distribution with a laser scattering diffraction type particle size distribution measuring device (for example, LS 13 320 manufactured by Beckman Coulter, Inc.), and measuring a volume-based particle size distribution by using, for example, Fluid R. I. Real 1.333, Sample R. I. Real 1.54 Imaginary 0 as an optical model.

In one embodiment, the solid carrier is porous, and has a specific surface area of preferably 50 $m^2/g$ or more and more preferably 80 $m^2/g$ or more, and preferably 150 $m^2/g$ or less and more preferably 130 $m^2/g$ or less, and is, for example, preferably 50 to 150 $m^2/g$ and more preferably 80 to 130 $m^2/g$. In this regard, when the specific surface area is less than 50 $m^2/g$, the binding capacity may decrease in some cases, and on the other hand, when the specific surface area exceeds 150 $m^2/g$, the carrier is broken under a high flow rate due to the poor strength of the carrier, and the column pressure may increase in some cases. In this regard, the expression "specific surface area" in the present specification means a value obtained by dividing the surface area of pores having a pore diameter of 10 to 5000 nm obtained by a mercury porosimeter by the particle dry weight.

In one embodiment, the solid carrier has a volume average pore diameter of preferably 100 nm or more and 1500 nm or less. For example, in a case where the carrier is a synthetic polymer, the volume average pore diameter is preferably 100 nm or more and more preferably 200 nm or more, and preferably 400 nm or less and more preferably 300 nm or less, and is, for example, preferably 100 to 400 nm and more preferably 200 to 300 nm. For example, in a case where the carrier is a polysaccharide, the volume average pore diameter is preferably 500 nm or more and more preferably 800 nm or more, and preferably 1500 nm or less and more preferably 1400 nm or less, and is, for example, preferably 500 to 1500 nm and more preferably 800 to 1400 nm. In this regard, when the volume average pore diameter is less than 100 nm, the binding capacity under a high flow rate may remarkably decrease in some cases, and on the other hand, when the volume average pore diameter exceeds 1500 nm, the binding capacity may decrease in some cases regardless of the flow rate. In this regard, the expression "volume average pore diameter" in the present specification means a volume average pore diameter of the pores having a pore diameter of 10 to 5000 nm obtained by a mercury porosimeter.

In a case where the solid carrier satisfies the particle diameter, specific surface area, and pore diameter distribution in the above ranges, respectively, the balance between the gap between particles serving as a flow path of a solution to be purified and relatively large pore diameter in a particle, and the bound surface area of the molecule to be purified is optimized, and the binding capacity under a high flow rate is maintained at a high level.

The material for the solid carrier is, for example, a polymer having a hydrophilic surface, and for example, a polymer having a hydroxy group (—OH), a carboxy group (—COOH), an aminocarbonyl group (—CONH$_2$, or N-substituted type), an amino group (—NH$_2$, or substituted type), or an oligo- or polyethyleneoxy group on the outer surface (and also on the inner surface if present) by hydrophilization treatment. In one embodiment, the polymer can be a synthetic polymer such as polymethacrylate, polyacrylamide, polystyrene, or a polyvinyl alcohol-based polymer, and is preferably a synthetic polymer such as a copolymer crosslinked with a polyfunctional monomer such as a polyfunctional (meth)acrylate, or divinylbenzene. Such a synthetic polymer is easily produced by a known method (see, for example, the method disclosed in J. MATER. CHEM 1991, 1(3): 371-374). Alternatively, a commercially available product such as TOYOPEARL (manufactured by Tosoh Corporation) may also be used. The polymers in other embodiments are polysaccharides such as dextran, starch, cellulose, pullulan, and agarose. Such polysaccharides are easily produced by a known method (see, for example, the method disclosed in JP 4081143 B). Alternatively, a commercially available product such as SEPHAROSE (manufactured by GE Healthcare Bio-Science) may also be used. The polymers in other embodiments may also be inorganic carriers such as silica, and zirconium oxide.

In one embodiment, as one specific example of the porous particles to be used as the solid carrier, for example, porous organic polymer particles containing a copolymer of 20 to 50% by mass of crosslinkable vinyl monomer, and 3 to 80% by mass of epoxy group-containing vinyl monomer or 20 to 80% by mass of diol group-containing vinyl monomer, and having a particle diameter of 20 to 80 µm, a specific surface area of 50 to 150 $m^2/g$, and a volume average pore diameter of 100 to 400 nm can be included.

In this regard, the infiltration volume (pore volume) of the pores having a pore diameter of 10 to 5000 nm when the solid carrier is measured by a mercury porosimeter is preferably 1.3 mL/g or more and 7.0 mL/g or less. For example, in a case where the carrier is a synthetic polymer, the pore volume is preferably 1.3 mL/g or more, and preferably 7.0 mL/g or less, more preferably 5.0 mL/g or less, and furthermore preferably 2.5 mL/g or less, and is, for example, preferably 1.3 to 7.0 mL/g, more preferably 1.3 to 5.0 mL/g, and furthermore preferably 1.3 to 2.5 mL/g. Further, for example, in a case where the carrier is a polysaccharide, the pore volume is preferably 3.0 to 6.0 mL/g.

As the method for binding a ligand (that is, the immunoglobulin-binding protein according to the present invention) to the solid carrier, a general method for immobilizing a protein on a carrier can be used. Examples of the general method include a method wherein a carrier having a carboxy group is used, and the carboxy group is activated by N-hydroxysuccinimide to react with an amino group of a ligand; a method wherein a carrier having an amino group or a carboxy group is used and the amino group or the carboxy group is reacted with a carboxy group or an amino group of a ligand in the presence of a dehydration condensation agent such as a water-soluble carbodiimide to form an amide bond; a method wherein a carrier having a hydroxyl group is used, and the hydroxyl group is activated with a cyanogen halide such as cyanogen bromide to react with an amino group of a ligand; a method wherein a hydroxyl group of a carrier is tosylated or tresylated to reacted with an amino group of a ligand; a method wherein an epoxy group is introduced into a carrier by, for example, bisepoxide or epichlorohydrin, and reacted with an amino group, a hydroxyl group, or a thiol group of a ligand; and a method wherein a carrier having an epoxy group is used, and the epoxy group is reacted with an amino group, a hydroxyl group, or a thiol group of a ligand. Among the above methods, from the viewpoint of the stability in an aqueous solution with which reaction is carried out, a method wherein a ligand is bound via an epoxy group is desirable.

A hydroxyl group that is a ring-opened epoxy group generated by ring opening of an epoxy group makes the surface of a carrier hydrophilic, prevents non-specific adsorption of, for example, proteins, and further plays a role in improving the toughness of the carrier in water and in preventing the carrier from breaking under a high flow rate. Accordingly, in a case where a residual epoxy group that is not bound to a ligand is present in the carrier on which the ligand has been immobilized, it is preferable to open the ring of the residual epoxy group. An example of the method for ring opening of the epoxy group in a carrier includes a method wherein the carrier is stirred by heating or at room temperature with an acid or alkali in a water solvent. Further, the ring-opening of the epoxy group may be performed with a blocking agent having a mercapto group such as mercaptoethanol or thioglycerol, or a blocking agent having an amino group such as monoethanolamine. A more preferable ring-opened epoxy group is a ring-opened epoxy group obtained by ring opening of an epoxy group contained in the carrier with thioglycerol. There are advantages that thioglycerol is less toxic than mercaptoethanol as a raw material, and that an epoxy ring-opened group to which thioglycerol has been added has non-specific adsorption lower than that of and further has dynamic binding amount higher than that of a ring-opened group by the blocking agent having an amino group.

If necessary, a molecule (spacer) having any length may be introduced between a solid carrier and a ligand. Examples of the spacer include a polymethylene chain, a polyethylene glycol chain, and a saccharide.

The affinity carrier according to the present invention has a ligand having improved alkali resistance, and therefore, there is no significant decrease in the performance also on, for example, washing under an alkaline condition for repeated use of the carrier in affinity purification (for example, washing by using an alkaline solution such as 0.01 to 1.0 M sodium hydroxide).

4. Method for Isolating Antibody or Fragment Thereof

A method for isolating an antibody or a fragment thereof (hereinafter, simply referred to as an antibody) according to one embodiment of the present invention will be described. The method for isolating an antibody according to the present embodiment suitably includes a step of passing a sample containing antibodies through an affinity carrier on which the immunoglobulin-binding protein according to the present invention is immobilized and allowing the antibodies to adsorb onto the carrier (first step), and a step of eluting the antibodies from the carrier (second step), and preferably further includes a step of washing the carrier with an alkaline solution after the second step (third step).

In the first step, a sample containing antibodies is passed through, for example, a column packed with the affinity carrier according to the present invention under the condition that the antibodies are adsorbed on a ligand (the immunoglobulin-binding protein according to the present invention). In the first step, most of the substances other than the antibodies in the sample pass through the column without being adsorbed to the ligand. After this, if necessary, the carrier may be washed with a neutral buffer solution containing a salt such as NaCl in order to remove some substances that are weakly held by the ligand.

In the second step, an appropriate buffer solution with pH 2 to 5 is passed through the column to elute the antibodies adsorbed onto the ligand. By collecting this eluate, the antibodies can be isolated from the sample.

In order to increase the purity of antibodies, the antibodies contained in the eluate obtained in the second step may be further purified. The purification of the antibodies can be performed by using, for example, cation exchange chromatography, anion exchange chromatography, mix-mode chromatography, hydrophilic interaction chromatography, hydrophobic interaction chromatography, and size exclusion chromatography alone or in appropriate combination. For example, by subjecting the eluate obtained in the second step to cation exchange chromatography and then to anion exchange chromatography, the antibodies can be purified. The cation exchange chromatography can be performed by using, for example, SP-SEPHAROSE FF (manufactured by GE Healthcare Bio-Science), BioPro IEX S (manufactured by YMC CO., LTD.), or BioPro IEX SmartSep S (manufactured by YMC CO., LTD.). The anion exchange chromatography can be performed by using, for example, Q-SEPHAROSE FF (manufactured by GE Healthcare Bio-Science), BioPro IEX Q (manufactured by YMC CO., LTD.), or BioPro IEX SmartSep Q (manufactured by YMC CO., LTD.).

In the method for isolating an antibody according to the present embodiment, preferably, a third step is performed following the above second step. In the third step, the affinity carrier is washed (CIP washing) with an alkaline solution. Examples of the alkaline solution to be used in the third step include an aqueous sodium hydroxide solution, an aqueous potassium hydroxide solution, triethylamine, and tetrabutylammonium hydroxide. Further, the molar concentration of the alkali salt in the alkaline solution to be used in the third step has a lower limit value of 0.001 M or more, preferably 0.01 M or more, and more preferably 0.1 M or more, and has an upper limit value of 6.0 M or less, preferably 4.0 M or less, and more preferably 2.0 M or less. The pH of the alkaline solution to be used has a lower limit value of pH 11.0 or more, preferably pH 12.0 or more, and more preferably pH 12.5 or more, and has an upper limit value of pH 16.0 or less, preferably pH 15.5 or less, and more preferably pH 15.0 or less.

The affinity carrier according to the present invention stably retains the antibody binding activity even after the washing in the third step due to the improved alkali resistance of the protein ligand, and therefore, can be used repeatedly for antibody isolation.

In one embodiment of the method for isolating an antibody according to the present invention, the isolated antibodies are used as antibody drugs. Accordingly, in one embodiment, the present invention is to provide a method for producing an antibody drug using the affinity carrier according to the present invention. The procedure of the method is basically the same as the procedure of the method for isolating an antibody described above except that a sample containing the desired antibody drug is used.

EXAMPLES

Hereinafter, the present invention will be further described specifically referring to Examples. Further, the following description generally shows the embodiments of the present invention, and the present invention is not limited by such description without particular reasons.

Reference Example 1: Synthesis of Porous Particles (1) Into 360 g of pure water, 3.58 g of polyvinyl alcohol (PVA-217 manufactured by KURARAY CO., Ltd.) was added, the mixture was heated and stirred to dissolve the polyvinyl alcohol, and cooled, and then into the cooled mixture, 0.36 g of sodium dodecyl sulfate (manufactured by Wako Pure Chemical Industries, Ltd.), 0.36 g of sodium sulfate (manufactured by Wako Pure Chemical Industries, Ltd.), and 0.18 g of sodium nitrite (manufactured by Wako Pure Chemical Industries, Ltd.) were added and stirred to prepare an aqueous solution S.

(2) A monomer composition comprising 12.00 g of glycidyl methacrylate (manufactured by Mitsubishi Chemical Corporation) and 1.33 g of divinylbenzene (manufactured by Nippon Steel Chemical Co., Ltd.) was dissolved in 24.43 g of diisobutyl ketone (manufactured by Mitsui Chemicals, Inc.) to prepare a monomer solution.

(3) The whole amount of the aqueous solution S obtained in (1) was put into a separable flask, the flask was equipped with a thermometer, stirring blades, and a cooling pipe, and set in a warm water bath, and the stirring was started under a nitrogen atmosphere. The whole amount of the monomer solution obtained in (2) was put into the separable flask, and the flask was heated in the warm water bath. When the internal temperature reached 85° C., 0.53 g of 2,2'-azoisobutyronitrile (manufactured by Wako Pure Chemical Industries, Ltd.) was added.

(4) The reaction mixture obtained in (3) was stirred for 3 hours while maintaining the temperature at 86° C. Next, the reaction mixture was cooled, and then filtered, and the residue was washed with pure water and ethanol. The washed particles were dispersed in pure water, and the dispersion was decanted three times to remove small particles. Next, the resultant particles were dispersed in pure water so that the concentration of the particles was 10% by mass, and thus a porous particle (PB) dispersion was obtained.

Example 1: Preparation of Immunoglobulin-Binding Protein (PrAts-0 to 32)

Immunoglobulin-binding proteins PrAts-0 to 32 were obtained. PrAt-0 is an immunoglobulin-binding protein containing a homotetramer wherein A1V/G29A mutants (alkali resistance-improved mutants: Non Patent Literature 1) of the C domain (SEQ ID NO: 3) of Protein A are linked in series by peptide bonds. PrAts-1 to 32 are each a mutant wherein the mutation shown in Table 1 has been introduced into an immunoglobulin-binding domain of PrAt-0.

TABLE 1

| Immunoglobulin-binding protein | Parent domain | Introduced mutation | Mutant domain | Number of domains |
|---|---|---|---|---|
| PrAt-0 | SEQ ID NO: 3 | — | — | 4 |
| PrAt-1 | (A1V/G29A) | N3Q | SEQ ID NO: 7 | 4 |
| PrAt-2 | | Δ K4 | SEQ ID NO: 8 | 4 |
| PrAt-3 | | N6Q | SEQ ID NO: 9 | 4 |
| PrAt-4 | | N11Q | SEQ ID NO: 10 | 4 |
| PrAt-5 | | N3Q, N6Q, N11Q | SEQ ID NO: 11 | 4 |
| PrAt-6 | | E24D | SEQ ID NO: 12 | 4 |
| PrAt-7 | | E25D | SEQ ID NO: 13 | 4 |
| PrAt-8 | | S39K | SEQ ID NO: 14 | 4 |
| PrAt-9 | | S39R | SEQ ID NO: 15 | 4 |
| PrAt-10 | | A46D | SEQ ID NO: 16 | 4 |
| PrAt-11 | | A46E | SEQ ID NO: 17 | 4 |
| PrAt-12 | | A46K | SEQ ID NO: 18 | 4 |
| PrAt-13 | | A46R | SEQ ID NO: 19 | 4 |
| PrAt-14 | | K49R | SEQ ID NO: 20 | 4 |
| PrAt-15 | | K58R | SEQ ID NO: 21 | 4 |
| PrAt-16 | | Δ K58 | SEQ ID NO: 22 | 4 |
| PrAt-17 | | N3A, N11Q | SEQ ID NO: 23 | 4 |
| PrAt-18 | | N3D, N11Q | SEQ ID NO: 24 | 4 |
| PrAt-19 | | N6D, N11Q | SEQ ID NO: 25 | 4 |
| PrAt-20 | | N3D, N6D, N11Q | SEQ ID NO: 26 | 4 |
| PrAt-21 | | N3A, N6D, N11Q | SEQ ID NO: 27 | 4 |
| PrAt-22 | | N11Q, T23R | SEQ ID NO: 28 | 4 |
| PrAt-23 | | N11Q, T23L | SEQ ID NO: 29 | 4 |
| PrAt-24 | | N11Q, T23S | SEQ ID NO: 30 | 4 |
| PrAt-25 | | N11Q, K49R | SEQ ID NO: 31 | 4 |
| PrAt-26 | | N11Q, T23R, K49R | SEQ ID NO: 32 | 4 |
| PrAt-27 | | N11Q, T23L, K49R | SEQ ID NO: 33 | 4 |
| PrAt-28 | | N11Q, T23S, K49R | SEQ ID NO: 34 | 4 |
| PrAt-29 | | N11Q, K58R | SEQ ID NO: 35 | 4 |
| PrAt-30 | | T23R | SEQ ID NO: 36 | 4 |
| PrAt-31 | | T23L | SEQ ID NO: 37 | 4 |
| PrAt-32 | | T23S | SEQ ID NO: 38 | 4 |

Expression and purification of PrAts-0 to 32 were respectively performed as follows. *E. coli* BL21 (DE3) (manufactured by New England Biolabs, Inc.) was transformed by using each of the plasmids encoding PrAts-0 to 32. The obtained transformants were cultured in a eutrophic medium at 37° C. to reach the logarithmic growth phase. After that, isopropyl-β-thiogalactopyranoside (manufactured by Wako Pure Chemical Industries, Ltd.) at a final concentration of 1 mM was added to the medium, and further the culture was conducted at 37° C. for 4 hours to express the desired protein. Subsequently, the culture solution was centrifuged, and the supernatant was removed, 30 mM Tris buffer solution with pH 9.5 containing egg white-derived lysozyme (manufactured by Wako Pure Chemical Industries, Ltd.) and polyoxyethylene(10) octylphenyl ether (manufactured by Wako Pure Chemical Industries, Ltd.) were added into the obtained bacterial cells, and the bacterial cells were crushed. From the obtained cell lysate, a recombinant immunoglobulin-binding protein was purified by cation exchange chromatography (SP-SEPHAROSE FF, manufactured by GE Healthcare Bio-Science) and anion exchange chromatography (Q-SEPHAROSE FF, manufactured by GE Healthcare Bio-Science). The purified immunoglobulin-binding protein was dialyzed against 10 mM citrate buffer solution with pH 6.0. The purity of the recombinant-type immunoglobulin-binding protein confirmed by SDS-PAGE was 95% or more.

Example 2: Preparation of Immunoglobulin-Binding Proteins (PrAps-0 to 41)

Immunoglobulin-binding proteins PrAps-0 to 39 were obtained. PrAp-0 is an immunoglobulin-binding protein containing a homopentamer wherein A1V/G29A mutants of the C domain (SEQ ID NO: 3) of Protein A are linked in series by peptide bonds, and PrAp-21 is an immunoglobulin-binding protein wherein cysteine (C) is linked to the C-terminus of a homopentamer wherein A1V/G29A mutants of the C domain (SEQ ID NO: 3) of Protein A are linked in series by peptide bonds. PrAps-1 to 20 are each a mutant wherein the mutation shown in Table 2 has been introduced into an immunoglobulin-binding domain of PrAp-0, and PrAps-22 to 41 are each a mutant wherein the mutation shown in Table 3 has been introduced into an immunoglobulin-binding domain of PrAp-21.

TABLE 2

| Immunoglobulin-binding protein | Parent domain | Introduced mutation | Mutant domain | Number of domains | C-terminal tag |
|---|---|---|---|---|---|
| PrAp-0 | SEQ ID NO: 3 | — | — | 5 | — |
| PrAp-1 | (A1V/G29A) | N11Q | SEQ ID NO: 10 | 5 | — |
| PrAp-2 | | N3Q, N6Q, N11Q | SEQ ID NO: 11 | 5 | — |
| PrAp-3 | | K49R | SEQ ID NO: 20 | 5 | — |
| PrAp-4 | | K58R | SEQ ID NO: 21 | 5 | — |
| PrAp-5 | | N3A, N11Q | SEQ ID NO: 23 | 5 | — |
| PrAp-6 | | N3D, N11Q | SEQ ID NO: 24 | 5 | — |

TABLE 2-continued

| Immunoglobulin-binding protein | Parent domain | Introduced mutation | Mutant domain | Number of domains | C-terminal tag |
|---|---|---|---|---|---|
| PrAp-7 | | N6D, N11Q | SEQ ID NO: 25 | 5 | — |
| PrAp-8 | | N3D, N6D, N11Q | SEQ ID NO: 26 | 5 | — |
| PrAp-9 | | N3A, N6D, N11Q | SEQ ID NO: 27 | 5 | — |
| PrAp-10 | | N11Q, T23R | SEQ ID NO: 28 | 5 | — |
| PrAp-11 | | N11Q, T23L | SEQ ID NO: 29 | 5 | — |
| PrAp-12 | | N11Q, T23S | SEQ ID NO: 30 | 5 | — |
| PrAp-13 | | N11Q, K49R | SEQ ID NO: 31 | 5 | — |
| PrAp-14 | | N11Q, T23R, K49R | SEQ ID NO: 32 | 5 | — |
| PrAp-15 | | N11Q, T23L, K49R | SEQ ID NO: 33 | 5 | — |
| PrAp-16 | | N11Q, T23S, K49R | SEQ ID NO: 34 | 5 | — |
| PrAp-17 | | N11Q, K58R | SEQ ID NO: 35 | 5 | — |
| PrAp-18 | | T23R | SEQ ID NO: 36 | 5 | — |
| PrAp-19 | | T23L | SEQ ID NO: 37 | 5 | — |
| PrAp-20 | | T23S | SEQ ID NO: 38 | 5 | — |

TABLE 3

| Immunoglobulin-binding protein | Parent domain | Introduced mutation | Mutant domain | Number of domains | C-terminal tag |
|---|---|---|---|---|---|
| PrAp-21 | SEQ ID NO: 3 | — | — | 5 | C |
| PrAp-22 | (A1V/G29A) | N11Q | SEQ ID NO: 10 | 5 | C |
| PrAp-23 | | N3Q, N6Q, N11Q | SEQ ID NO: 11 | 5 | C |
| PrAp-24 | | K49R | SEQ ID NO: 20 | 5 | C |
| PrAp-25 | | K58R | SEQ ID NO: 21 | 5 | C |
| PrAp-26 | | N3A, N11Q | SEQ ID NO: 23 | 5 | C |
| PrAp-27 | | N3D, N11Q | SEQ ID NO: 24 | 5 | C |
| PrAp-28 | | N6D, N11Q | SEQ ID NO: 25 | 5 | C |
| PrAp-29 | | N3D, N6D, N11Q | SEQ ID NO: 26 | 5 | C |
| PrAp-30 | | N3A, N6D, N11Q | SEQ ID NO: 27 | 5 | C |
| PrAp-31 | | N11Q, T23R | SEQ ID NO: 28 | 5 | C |
| PrAp-32 | | N11Q, T23L | SEQ ID NO: 29 | 5 | C |
| PrAp-33 | | N11Q, T23S | SEQ ID NO: 30 | 5 | C |
| PrAp-34 | | N11Q, K49R | SEQ ID NO: 31 | 5 | C |
| PrAp-35 | | N11Q, T23R, K49R | SEQ ID NO: 32 | 5 | C |
| PrAp-36 | | N11Q, T23L, K49R | SEQ ID NO: 33 | 5 | C |
| PrAp-37 | | N11Q, T23S, K49R | SEQ ID NO: 34 | 5 | C |
| PrAp-38 | | N11Q, K58R | SEQ ID NO: 35 | 5 | C |
| PrAp-39 | | T23R | SEQ ID NO: 36 | 5 | C |
| PrAp-40 | | T23L | SEQ ID NO: 37 | 5 | C |
| PrAp-41 | | T23S | SEQ ID NO: 38 | 5 | C |

Expression and purification of PrAps-0 to 41 were performed in a similar manner as for PrAts-0 to 32. The purity of the recombinant-type immunoglobulin-binding protein confirmed by SDS-PAGE was 95% or more.

Example 3: Preparation of Immunoglobulin-Binding Proteins (PrAhs-0 to 41)

Immunoglobulin-binding proteins PrAhs-0 to 41 were obtained. PrAh-0 is an immunoglobulin-binding protein containing a homohexamer wherein A1V/G29A mutants of the C domain (SEQ ID NO: 3) of Protein A are linked in series by peptide bonds, and PrAh-21 is an immunoglobulin-binding protein wherein cysteine (C) is linked to the C-terminus of a homohexamer wherein A1V/G29A mutants of the C domain (SEQ ID NO: 3) of Protein A are linked in series by peptide bonds. PrAhs-1 to 20 are each a mutant wherein the mutation shown in Table 4 has been introduced into an immunoglobulin-binding domain of PrAh-0, and PrAhs-22 to 41 are each a mutant wherein the mutation shown in Table 5 has been introduced into an immunoglobulin-binding domain of PrAh-21.

TABLE 4

| Immunoglobulin-binding protein | Parent domain | Introduced mutation | Mutant domain | Number of domains | C-terminal tag |
|---|---|---|---|---|---|
| PrAh-0 | SEQ ID NO: 3 | — | — | 6 | — |
| PrAh-1 | (A1V/G29A) | N11Q | SEQ ID NO: 10 | 6 | — |
| PrAh-2 | | N3Q, N6Q, N11Q | SEQ ID NO: 11 | 6 | — |
| PrAh-3 | | K49R | SEQ ID NO: 20 | 6 | — |
| PrAh-4 | | K58R | SEQ ID NO: 21 | 6 | — |
| PrAh-5 | | N3A, N11Q | SEQ ID NO: 23 | 6 | — |
| PrAh-6 | | N3D, N11Q | SEQ ID NO: 24 | 6 | — |
| PrAh-7 | | N6D, N11Q | SEQ ID NO: 25 | 6 | — |
| PrAh-8 | | N3D, N6D, N11Q | SEQ ID NO: 26 | 6 | — |

TABLE 4-continued

| Immunoglobulin-binding protein | Parent domain | Introduced mutation | Mutant domain | Number of domains | C-terminal tag |
|---|---|---|---|---|---|
| PrAh-9 | | N3A, N6D, N11Q | SEQ ID NO: 27 | 6 | — |
| PrAh-10 | | N11Q, T23R | SEQ ID NO: 28 | 6 | — |
| PrAh-11 | | N11Q, T23L | SEQ ID NO: 29 | 6 | — |
| PrAh-12 | | N11Q, T23S | SEQ ID NO: 30 | 6 | — |
| PrAh-13 | | N11Q, K49R | SEQ ID NO: 31 | 6 | — |
| PrAh-14 | | N11Q, T23R, K49R | SEQ ID NO: 32 | 6 | — |
| PrAh-15 | | N11Q, T23L, K49R | SEQ ID NO: 33 | 6 | — |
| PrAh-16 | | N11Q, T23S, K49R | SEQ ID NO: 34 | 6 | — |
| PrAh-17 | | N11Q, K58R | SEQ ID NO: 35 | 6 | — |
| PrAh-18 | | T23R | SEQ ID NO: 36 | 6 | — |
| PrAh-19 | | T23L | SEQ ID NO: 37 | 6 | — |
| PrAh-20 | | T23S | SEQ ID NO: 38 | 6 | — |

TABLE 5

| Immunoglobulin-binding protein | Parent domain | Introduced mutation | Mutant domain | Number of domains | C-terminal tag |
|---|---|---|---|---|---|
| PrAh-21 | SEQ ID NO: 3 | — | — | 6 | C |
| PrAh-22 | (A1V/G29A) | N11Q | SEQ ID NO: 10 | 6 | C |
| PrAh-23 | | N3Q, N6Q, N11Q | SEQ ID NO: 11 | 6 | C |
| PrAh-24 | | K49R | SEQ ID NO: 20 | 6 | C |
| PrAh-25 | | K58R | SEQ ID NO: 21 | 6 | C |
| PrAh-26 | | N3A, N11Q | SEQ ID NO: 23 | 6 | C |
| PrAh-27 | | N3D, N11Q | SEQ ID NO: 24 | 6 | C |
| PrAh-28 | | N6D, N11Q | SEQ ID NO: 25 | 6 | C |
| PrAh-29 | | N3D, N6D, N11Q | SEQ ID NO: 26 | 6 | C |
| PrAh-30 | | N3A, N6D, N11Q | SEQ ID NO: 27 | 6 | C |
| PrAh-31 | | N11Q, T23R | SEQ ID NO: 28 | 6 | C |
| PrAh-32 | | N11Q, T23L | SEQ ID NO: 29 | 6 | C |
| PrAh-33 | | N11Q, T23S | SEQ ID NO: 30 | 6 | C |
| PrAh-34 | | N11Q, K49R | SEQ ID NO: 31 | 6 | C |
| PrAh-35 | | N11Q, T23R, K49R | SEQ ID NO: 32 | 6 | C |
| PrAh-36 | | N11Q, T23L, K49R | SEQ ID NO: 33 | 6 | C |
| PrAh-37 | | N11Q, T23S, K49R | SEQ ID NO: 34 | 6 | C |
| PrAh-38 | | N11Q, K58R | SEQ ID NO: 35 | 6 | C |
| PrAh-39 | | T23R | SEQ ID NO: 36 | 6 | C |
| PrAh-40 | | T23L | SEQ ID NO: 37 | 6 | C |
| PrAh-41 | | T23S | SEQ ID NO: 38 | 6 | C |

Expression and purification of PrAhs-0 to 41 were performed in a similar manner as for PrAts-0 to 32. The purity of the recombinant-type immunoglobulin-binding protein confirmed by SDS-PAGE was 95% or more.

Example 4: Preparation of Ligand-Immobilized Particles

Into 8 mg of the porous particles (PB) obtained in Reference Example 1, 450 µL of 0.1 M carbonic acid buffer solution (pH 8.8) containing 1.1 M sodium sulfate wherein 1.16 mg of PrAt-0 prepared in Example 1 had been dissolved was added, and the mixture was shaken at 25° C. for 5 hours to bind PrAt-0 to PB. The epoxy groups remaining on the particles were blocked by using thioglycerol, and then the particles were washed with 0.5 M NaOH and 0.1 M citrate buffer (pH 3.2) to obtain ligand-immobilized particles (PrAt-0/PB). In a similar procedure, ligand-immobilized particles (PrAts-1 to 32/PB) to which PrAts-1 to 32 were bound respectively were obtained. Further, ligand-immobilized particles (PrAps-0 to 41/PB) to which PrAps-0 to 41 were bound respectively were obtained in a similar procedure. Furthermore, ligand-immobilized particles (PrAhs-0 to 41/PB) to which PrAhs-0 to 41 were bound respectively were obtained in a similar procedure.

Example 5: Preparation of Immunoglobulin-Binding Proteins (PrAss-0 to 22)

Immunoglobulin-binding proteins PrAs-0 to 22 were obtained. PrAs-0 is an immunoglobulin-binding protein wherein a 6× histidine tag (HHHHHH sequence) is linked to the N-terminus of A1V/G29A mutant of the C domain (SEQ ID NO: 3) of Protein A. PrAss-1 to 22 are each a mutant wherein the mutation shown in Table 6 has been introduced into an immunoglobulin-binding domain of PrAs-0.

TABLE 6

| Immunoglobulin-binding protein | Parent domain | Introduced mutation | Mutant domain | Number of domains | N-terminal tag |
|---|---|---|---|---|---|
| PrAs-0 | SEQ ID NO: 3 | — | — | 1 | HHHHHH |
| PrAs-1 | (A1V/G29A) | N11A | SEQ ID NO: 39 | 1 | |

TABLE 6-continued

| Immunoglobulin-binding protein | Parent domain | Introduced mutation | Mutant domain | Number of domains | N-terminal tag |
|---|---|---|---|---|---|
| PrAs-2  |  | N11R | SEQ ID NO: 40 | 1 |  |
| PrAs-3  |  | N11D | SEQ ID NO: 41 | 1 |  |
| PrAs-4  |  | N11C | SEQ ID NO: 42 | 1 |  |
| PrAs-5  |  | N11Q | SEQ ID NO: 10 | 1 |  |
| PrAs-6  |  | N11E | SEQ ID NO: 43 | 1 |  |
| PrAs-7  |  | N11H | SEQ ID NO: 44 | 1 |  |
| PrAs-8  |  | N11I | SEQ ID NO: 45 | 1 |  |
| PrAs-9  |  | N11L | SEQ ID NO: 46 | 1 |  |
| PrAs-10 |  | N11K | SEQ ID NO: 47 | 1 |  |
| PrAs-11 |  | N11M | SEQ ID NO: 48 | 1 |  |
| PrAs-12 |  | N11F | SEQ ID NO: 49 | 1 |  |
| PrAs-13 |  | N11T | SEQ ID NO: 50 | 1 |  |
| PrAs-14 |  | N11W | SEQ ID NO: 51 | 1 |  |
| PrAs-15 |  | N11Y | SEQ ID NO: 52 | 1 |  |
| PrAs-16 |  | N11V | SEQ ID NO: 53 | 1 |  |
| PrAs-17 |  | N11G | SEQ ID NO: 54 | 1 |  |
| PrAs-18 |  | N11P | SEQ ID NO: 55 | 1 |  |
| PrAs-19 |  | N11S | SEQ ID NO: 56 | 1 |  |
| PrAs-20 |  | T23R | SEQ ID NO: 36 | 1 |  |
| PrAs-21 |  | T23L | SEQ ID NO: 37 | 1 |  |
| PrAs-22 |  | T23S | SEQ ID NO: 38 | 1 |  |

Expression and purification of PrAss-0 to 22 were performed in a similar manner as for PrAts-0 to 32 except that the recombinant immunoglobulin-binding protein was purified by affinity chromatography (HisTrap FF, manufactured by GE Healthcare Bio-Science). The purity of the recombinant-type immunoglobulin-binding protein confirmed by SDS-PAGE was 95% or more.

Test Example 1

The ligand-immobilized particles PrAts-1 to 29/PB each containing a mutant domain prepared in Example 4 were evaluated for the relative alkali resistance to the ligand-immobilized particles PrAt-0 containing the parent domain.

(1) Measurement of Static Binding Capacity (SBC)

To 2 mg of ligand-immobilized particles (PrAt-0/PB), 400 μL of 20 mM phosphate buffer (pH 7.5) containing 2.0 mg of IgG was added, and the obtained mixture was incubated for 30 minutes. Next, the particles were washed with 400 μL of 20 mM phosphate buffer (pH 7.5), and then 400 μL of 50 mM sodium citrate buffer (pH 2.5) was added to the washed particles, and the eluate containing IgG was recovered. The amount of IgG in the eluate was calculated by absorbance measurement, and the static binding capacity (SBC) of PrAt-0/PB was determined from the amount of eluted IgG and the carrier volume. In a similar procedure, the SBC of each of PrAts-1 to 29/PB was determined. Further, in a similar procedure, the SBC of each of PrAhs-21 to 41/PB was determined.

(2) Evaluation for Alkali Resistance: PrAts-1 to 29

After 2 mg of ligand-immobilized particles (PrAt-0/PB) was equilibrated with 1.0 M NaOH, the equilibrated particles were incubated for 24 hours. Next, after the particles were equilibrated with 20 mM phosphate buffer (pH 7.5), 400 μL of 20 mM phosphate buffer (pH 7.5) containing 2.0 mg of IgG was added to the particles, and the obtained mixture was incubated for 30 minutes. Subsequently, the particles were washed with 400 μL of 20 mM phosphate buffer (pH 7.5), and then 400 μL of 50 mM sodium citrate buffer (pH 2.5) was added to the washed particles, and the eluate containing IgG was recovered. The amount of IgG in the eluate was calculated by absorbance measurement, and the SBC of PrAt-0/PB exposed to alkali was determined from the amount of eluted IgG and the carrier volume. In a similar procedure, the SBC of each of PrAts-1 to 29/PB exposed to alkali was determined. For the ligand-immobilized particles, the relative value (SBC retention ratio) of the SBC after alkali exposure to the SBC determined in (1) was calculated, and then the relative alkali resistance (%) of each of the ligand-immobilized particles (PrAts-1 to 29) to PrAt-0 was calculated in accordance with the following equation.

Relative alkali resistance (%)=(SBC retention ratio of $PrAt\text{-}N$ ($N$=1 to 29))/(SBC retention ratio of PrAt-0)×100

(3) Evaluation for alkali resistance: PrAhs-22 to 38

The SBC of each of PrAhs-21 to 38/PB exposed to alkali was determined by a similar procedure as in (2), and the relative alkali resistance (%) of each of PrAhs-22 to 38 to PrAh-21 was calculated.

(4) Evaluation for alkali resistance: PrAhs-39 to 41

Ligand-immobilized particles (PrAhs-21 and 39 to 41/PB) were equilibrated by a similar procedure as in (2) except that 0.5 M NaOH was used in place of 1.0 M NaOH, and then the incubation was performed for 24 hours. After that, the SBC of each of PrAhs-21 and 39 to 41/PB exposed to alkali was determined by a similar procedure as in (2), and the relative alkali resistance (%) of each of PrAhs-39 to 41 to PrAh-21 was calculated.

Measurement results of the SBC measured in (1) and the relative alkali resistance measured in (2) to (4) were shown in Tables 7 to 9. The SBC of each of PrAts-1 to 29/PB was not significantly different from that of PrAt-0/PB. On the other hand, the relative alkali resistance of each of PrAts-1 to 29/PB was improved by 14 to 64% as compared with that of PrAt-0/PB. Further, the SBC of each of PrAhs-22 to 38/PB was not significantly different from that of PrAh-21/PB, but each relative alkali resistance was improved by 28 to 69% as compared with that of PrAh-21/PB. Furthermore, the SBC of each of PrAhs-39 to 41/PB was not significantly different from that of PrAh-21/PB, but each relative alkali resistance was improved by 22 to 26% as compared with that of PrAh-21/PB. From these results, it was indicated that the immunoglobulin-binding proteins of Examples 1 to 3 each containing a mutant domain have higher alkali resistance than that before the mutation introduction, and the antibody binding activity can be retained even after being placed in a relatively severe condition, that is, being exposed to 1.0 M or 0.5 M sodium hydroxide for 24 hours.

TABLE 7

| Ligand-immobilized particle | SBC (mg/mL-particle) | Relative alkali resistance (%) |
| --- | --- | --- |
| PrAt-0/PB | 65.9 | (100) |
| PrAt-1/PB | 69.6 | 114 |
| PrAt-2/PB | 52.7 | 155 |
| PrAt-3/PB | 65.7 | 118 |
| PrAt-4/PB | 69.3 | 144 |
| PrAt-5/PB | 75.8 | 154 |
| PrAt-6/PB | 67.8 | 125 |
| PrAt-7/PB | 76.7 | 124 |
| PrAt-8/PB | 67.2 | 131 |
| PrAt-9/PB | 64.4 | 135 |
| PrAt-10/PB | 69.5 | 134 |
| PrAt-11/PB | 68.0 | 125 |
| PrAt-12/PB | 63.2 | 164 |
| PrAt-13/PB | 70.3 | 156 |
| PrAt-14/PB | 68.7 | 130 |
| PrAt-15/PB | 75.1 | 127 |
| PrAt-16/PB | 68.6 | 128 |
| PrAt-17/PB | 67.2 | 153 |
| PrAt-18/PB | 69.9 | 152 |
| PrAt-19/PB | 66.4 | 148 |
| PrAt-20/PB | 68.1 | 158 |
| PrAt-21/PB | 67.4 | 160 |
| PrAt-22/PB | 67.3 | 151 |
| PrAt-23/PB | 68.2 | 154 |
| PrAt-24/PB | 64.6 | 147 |
| PrAt-25/PB | 69.7 | 149 |
| PrAt-26/PB | 69.5 | 160 |
| PrAt-27/PB | 70.0 | 161 |
| PrAt-28/PB | 65.3 | 153 |
| PrAt-29/PB | 72.1 | 150 |

TABLE 8

| Ligand-immobilized particle | SBC (mg/mL-particle) | Relative alkali resistance (%) |
| --- | --- | --- |
| PrAh-21/PB | 77.8 | (100) |
| PrAh-22/PB | 76.2 | 147 |
| PrAh-23/PB | 79.1 | 157 |
| PrAh-24/PB | 71.5 | 136 |
| PrAh-25/PB | 80.2 | 128 |
| PrAh-26/PB | 76.9 | 156 |
| PrAh-27/PB | 77.8 | 153 |
| PrAh-28/PB | 77.3 | 152 |
| PrAh-29/PB | 80.7 | 156 |
| PrAh-30/PB | 78.9 | 169 |
| PrAh-31/PB | 75.5 | 156 |
| PrAh-32/PB | 79.0 | 157 |
| PrAh-33/PB | 76.2 | 150 |
| PrAh-34/PB | 78.4 | 155 |
| PrAh-35/PB | 78.1 | 163 |
| PrAh-36/PB | 77.6 | 166 |
| PrAh-37/PB | 75.0 | 157 |
| PrAh-38/PB | 79.4 | 151 |

TABLE 9

| Ligand-immobilized particle | SBC (mg/mL-particle) | Relative alkali resistance (%) |
| --- | --- | --- |
| PrAh-21/PB | 77.8 | (100) |
| PrAh-39/PB | 75.7 | 122 |
| PrAh-40/PB | 77.6 | 122 |
| PrAh-41/PB | 83.1 | 126 |

Test Example 2

The immunoglobulin-binding proteins PrAss-1 to 19 each containing a mutant domain prepared in Example 5 were evaluated for the relative alkali resistance to the immunoglobulin-binding protein PrAs-0 containing the parent domain.

(1) Preparation of Sample Solution 0.13 mg of each of the immunoglobulin-binding proteins (PrAss-0 and 1 to 19) was incubated in 1.0 M aqueous sodium hydroxide solution. Immediately after the start of the incubation or 24 hours after the start of the incubation, each solution was neutralized with 1.0 M citric acid. Next, the neutralized solution was diluted so as to have a protein concentration of 10 µg/mL by using D-PBS buffer containing 0.1% bovine serum-derived albumin (manufactured by Wako Pure Chemical Industries, Ltd.) and 0.02% Triton X-100 (manufactured by Wako Pure Chemical Industries, Ltd.), and thus a sample solution was prepared. With respect to the sample solution, the sample solution obtained by neutralizing PrAs—N (N=0 to 19) in sodium hydroxide immediately after the start of the incubation was defined as PrAs—Na, and the sample solution obtained by neutralizing the PrAs—N in sodium hydroxide 24 hours after the start of the incubation was defined as PrAs—Nb.

(2) Preparation of IgG Binding Biosensor 1.0 mg of IgG was reacted with 3.9 µg of EZ-Link NHS-PEG4-Biotin (manufactured by Thermo Fisher Scientific) to biotinylate the IgG. The biotinylated IgG was brought into contact with a streptavidin biosensor (manufactured by Pall ForteBio) by using an Octet RED 96e system (manufactured by Pall ForteBio), and was immobilized on the sensor.

(3) Evaluation for Alkali Resistance

The IgG binding biosensor was brought into contact with a sample solution by using an Octet RED 96e system, and an immunoglobulin-binding protein was bound to the IgG on the sensor. The binding rate was determined from the sensorgrams, and the relative value (binding rate retaining ratio) of the binding rate of PrAs—Nb to the binding rate of PrAs—Na was calculated. Next, the relative alkali resistance (%) of each of the immunoglobulin-binding proteins (PrAss-0 to 19) to PrAs-0 was calculated in accordance with the following equation.

Relative alkali resistance (%)={binding rate retaining ratio of (*PrAs-N* (*N*=1 to 19))/(binding rate retaining ratio of *PrAs*-0)}×100

Binding rate retaining ratio of *PrAs-N* (*N*=0 to 19)= (binding rate of *PrAs-N* (*N*=0 to 19)*b*)/(binding rate of *PrAs-N* (*N*=0 to 19)*a*)

The measurement results of the relative alkali resistance are shown in Table 10. The relative alkali resistance of each of PrAss-17 to 19 was lower than that of PrAs-0, but the relative alkali resistance of each of PrAss-1 to 16 was improved by 60 to 338% as compared with that of PrAs-0. From these results, it was indicated that each of the immunoglobulin-binding proteins PrAss-1 to 16 containing a mutant domain has higher alkali resistance as compared with that before the mutation introduction, and the antibody binding activity can be retained even after being placed in a relatively severe condition, that is, being exposed to 1.0 M sodium hydroxide for 24 hours.

TABLE 10

| Immunoglobulin-binding protein | Relative alkali resistance (%) |
|---|---|
| PrAs-0 | (100) |
| PrAs-1 | 368 |
| PrAs-2 | 331 |
| PrAs-3 | 176 |
| PrAs-4 | 160 |
| PrAs-5 | 375 |
| PrAs-6 | 342 |
| PrAs-7 | 362 |
| PrAs-8 | 438 |
| PrAs-9 | 348 |
| PrAs-10 | 370 |
| PrAs-11 | 429 |
| PrAs-12 | 306 |
| PrAs-13 | 170 |
| PrAs-14 | 281 |
| PrAs-15 | 368 |

TABLE 10-continued

| Immunoglobulin-binding protein | Relative alkali resistance (%) |
|---|---|
| PrAs-16 | 409 |
| PrAs-17 | 94 |
| PrAs-18 | 19 |
| PrAs-19 | 84 |

Test Example 3

For each of the immunoglobulin-binding proteins (PrAss-0 and 20 to 22) prepared in Example 5, the alkali resistance was calculated by a similar procedure as in Test Example 2 except that the obtained mixture was incubated in 0.5 M aqueous sodium hydroxide solution. The measurement results of the relative alkali resistance are shown in Table 11. Since the relative alkali resistance of each of PrAss-20 to 22 was improved by 21 to 31% as compared with that of PrAs-0, it was indicated that the alkali resistance was higher as compared with that before the mutation introduction.

TABLE 11

| Immunoglobulin-binding protein | Relative alkali resistance (%) |
|---|---|
| PrAs-0 | (100) |
| PrAs-20 | 121 |
| PrAs-21 | 125 |
| PrAs-22 | 131 |

The invention claimed is:

1. An immunoglobulin-binding protein, comprising:
a polypeptide chain consisting of an amino acid sequence having at least 85% identity to an amino acid sequence represented by any one of SEQ ID NOs: 1 to 6, 57-59 and 61-62, wherein said amino acid sequence having at least 85% identity to any one of SEQ ID NOS: 1 to 6, 57-59 and 61-62 having a substitution of Asn with Gln at a position corresponding to position 11 of the amino acid sequence represented by SEQ ID NO: 1, 2, 3, 5, or at position 6 of the amino acid sequence represented by SEQ ID No. 4, or at position 9 of the amino acid sequence represented by SEQ ID No. 6, or at position 7 of the amino acid sequence represented by SEQ ID No. 57, 58, 59, 61, 62 and optionally having at least one mutation selected from the group consisting of (a) to (f):

(a) substitution of an amino acid residue at at least one position selected from the group consisting of positions corresponding to positions 3 and 6 of the amino acid sequence represented by SEQ ID NO: 3 with another amino acid residue, deletion of the amino acid residue at the at least one position, or insertion of another amino acid residue into a position in front of or behind the at least one position;

(b) substitution of an amino acid residue at at least one position selected from the group consisting of positions corresponding to positions 24 and 25 of the amino acid sequence represented by SEQ ID NO: 3 with another amino acid residue, deletion of the amino acid residue at the at least one position, or insertion of another amino acid residue into a position in front of or behind the at least one position;
(c) substitution of an amino acid residue at a position corresponding to position 39 of the amino acid sequence represented by SEQ ID NO: 3 with another amino acid residue, deletion of the amino acid residue at the position corresponding to position 39, or insertion of another amino acid residue into a position in front of or behind the position corresponding to position 39;
(d) substitution of an amino acid residue at a position corresponding to position 46 of the amino acid sequence represented by SEQ ID NO: 3 with another amino acid residue, deletion of the amino acid residue at the position corresponding to position 46, or insertion of another amino acid residue into a position in front of or behind the position corresponding to position 46;
(e) substitution of an amino acid residue at at least one position selected from the group consisting of positions corresponding to positions 4, 49, and 58 of the amino acid sequence represented by SEQ ID NO: 3 with another amino acid residue, deletion of the amino acid residue at the at least one position, or insertion of another amino acid residue into a position in front of or behind the at least one position; and
(f) substitution of an amino acid residue at a position corresponding to position 23 of the amino acid sequence represented by SEQ ID NO: 3 with another amino acid residue, deletion of the amino acid residue at the position corresponding to position 23, or insertion of another amino acid residue into a position in front of or behind the position corresponding to position 23.

2. The protein of claim 1, wherein the polypeptide chain is a polypeptide chain consisting of an amino acid sequence having at least 85% identity to the amino acid sequence represented by SEQ ID NO: 3 and having the at least one mutation.

3. The protein of claim 1, wherein the at least one mutation is selected from the group consisting of:
(a1) substitution of Asn with Gln at a position corresponding to position 3 of the amino acid sequence represented by SEQ ID NO: 3;
(a2) substitution of Asn with Ala at a position corresponding to position 3 of the amino acid sequence represented by SEQ ID NO: 3;
(a3) substitution of Asn with Asp at a position corresponding to position 3 of the amino acid sequence represented by SEQ ID NO: 3;
(a4) substitution of Asn with Gln at a position corresponding to position 6 of the amino acid sequence represented by SEQ ID NO: 3;
(a5) substitution of Asn with Ala at a position corresponding to position 6 of the amino acid sequence represented by SEQ ID NO: 3;
(a6) substitution of Asn with Asp at a position corresponding to position 6 of the amino acid sequence represented by SEQ ID NO: 3;
(b1) substitution of Glu with Asp at a position corresponding to position 24 of the amino acid sequence represented by SEQ ID NO: 3;
(b2) substitution of Glu with Asp at a position corresponding to position 25 of the amino acid sequence represented by SEQ ID NO: 3;
(c1) substitution of Ser with Lys at a position corresponding to position 39 of the amino acid sequence represented by SEQ ID NO: 3;
(c2) substitution of Ser with Arg at a position corresponding to position 39 of the amino acid sequence represented by SEQ ID NO: 3;
(d1) substitution of Ala with Asp at a position corresponding to position 46 of the amino acid sequence represented by SEQ ID NO: 3;
(d2) substitution of Ala with Glu at a position corresponding to position 46 of the amino acid sequence represented by SEQ ID NO: 3;
(d3) substitution of Ala with Lys at a position corresponding to position 46 of the amino acid sequence represented by SEQ ID NO: 3;
(d4) substitution of Ala with Arg at a position corresponding to position 46 of the amino acid sequence represented by SEQ ID NO: 3;
(e1) deletion of Lys at a position corresponding to position 4 of the amino acid sequence represented by SEQ ID NO: 3;
(e2) substitution of Lys with Arg at a position corresponding to position 49 of the amino acid sequence represented by SEQ ID NO: 3;
(e3) deletion of Lys at a position corresponding to position 58 of the amino acid sequence represented by SEQ ID NO: 3;
(e4) substitution of Lys with Arg at a position corresponding to position 58 of the amino acid sequence represented by SEQ ID NO: 3;
(f1) substitution of Thr with Arg at a position corresponding to position 23 of the amino acid sequence represented by SEQ ID NO: 3;
(f2) substitution of Thr with Leu at a position corresponding to position 23 of the amino acid sequence represented by SEQ ID NO: 3; and
(f3) substitution of Thr with Ser at a position corresponding to position 23 of the amino acid sequence represented by SEQ ID NO: 3.

4. The protein of claim 3, wherein the at least one mutation is selected from the group consisting of:
(a1) substitution of Asn with Gln at a position corresponding to position 3 of the amino acid sequence represented by SEQ ID NO: 3;
(a2) substitution of Asn with Ala at a position corresponding to position 3 of the amino acid sequence represented by SEQ ID NO: 3;
(a3) substitution of Asn with Asp at a position corresponding to position 3 of the amino acid sequence represented by SEQ ID NO: 3;
(a4) substitution of Asn with Gln at a position corresponding to position 6 of the amino acid sequence represented by SEQ ID NO: 3;
(a5) substitution of Asn with Ala at a position corresponding to position 6 of the amino acid sequence represented by SEQ ID NO: 3;
(a6) substitution of Asn with Asp at a position corresponding to position 6 of the amino acid sequence represented by SEQ ID NO: 3;
(a23) substitution of Asns with Glns at positions corresponding to positions 3 and 6 of the amino acid sequence represented by SEQ ID NO: 3;

(a24) substitution of Asn with Ala at a position corresponding to position 3 of the amino acid sequence represented by SEQ ID NO: 3;
(a25) substitution of Asn with Asp at a position corresponding to position 3 of the amino acid sequence represented by SEQ ID NO: 3;
(a26) substitution of Asn with Asp at a position corresponding to position 6 of the amino acid sequence represented by SEQ ID NO: 3;
(a27) substitution of Asn with Asp at a position corresponding to position 3, and substitution of Asn with Asp at a position corresponding to position 6 of the amino acid sequence represented by SEQ ID NO: 3;
(a28) substitution of Asn with Ala at a position corresponding to position 3, and substitution of Asn with Asp at a position corresponding to position 6 of the amino acid sequence represented by SEQ ID NO: 3;
(b1) substitution of Glu with Asp at a position corresponding to position 24 of the amino acid sequence represented by SEQ ID NO: 3;
(b2) substitution of Glu with Asp at a position corresponding to position 25 of the amino acid sequence represented by SEQ ID NO: 3;
(c1) substitution of Ser with Lys at a position corresponding to position 39 of the amino acid sequence represented by SEQ ID NO: 3;
(c2) substitution of Ser with Arg at a position corresponding to position 39 of the amino acid sequence represented by SEQ ID NO: 3;
(d1) substitution of Ala with Asp at a position corresponding to position 46 of the amino acid sequence represented by SEQ ID NO: 3;
(d2) substitution of Ala with Glu at a position corresponding to position 46 of the amino acid sequence represented by SEQ ID NO: 3;
(d3) substitution of Ala with Lys at a position corresponding to position 46 of the amino acid sequence represented by SEQ ID NO: 3;
(d4) substitution of Ala with Arg at a position corresponding to position 46 of the amino acid sequence represented by SEQ ID NO: 3;
(e1) deletion of Lys at a position corresponding to position 4 of the amino acid sequence represented by SEQ ID NO: 3;
(e2) substitution of Lys with Arg at a position corresponding to position 49 of the amino acid sequence represented by SEQ ID NO: 3;
(e3) deletion of Lys at a position corresponding to position 58 of the amino acid sequence represented by SEQ ID NO: 3;
(e4) substitution of Lys with Arg at a position corresponding to position 58 of the amino acid sequence represented by SEQ ID NO: 3;
(f1) substitution of Thr with Arg at a position corresponding to position 23 of the amino acid sequence represented by SEQ ID NO: 3;
(f2) substitution of Thr with Leu at a position corresponding to position 23 of the amino acid sequence represented by SEQ ID NO: 3;
(f3) substitution of Thr with Ser at a position corresponding to position 23 of the amino acid sequence represented by SEQ ID NO: 3;
(g6) a combination of (f1) and (e2);
(g7) a combination of (f2) and (e2); and
(g8) a combination of (f3) and (e2).

5. The protein of claim 1, wherein the at least one mutation comprises substitution of amino acid residues at positions corresponding to at least two of positions 3, 6, 24, 25, 39, 46, 4, 49, 58, and 23 of the amino acid sequence represented by SEQ ID NO: 3 with other amino acid residues, deletion of the amino acid residues at the positions, or insertion of other amino acid residues into positions in front of or behind the positions.

6. The protein of claim 5, wherein the at least one mutation is any one of the (a23) to (a28), or a combination of any one of the (a1) to (a6), (a23) to (a28) and any one or more of the (b1) to (f3).

7. The protein of claim 1, wherein the identity of the amino acid sequence is at least 90%.

8. The protein of claim 1, wherein the polypeptide chain further comprises substitution of an amino acid residue at a position corresponding to position 1 of the amino acid sequence represented by SEQ ID NO: 3 with Val and/or substitution of an amino acid residue at a position corresponding to position 29 of the amino acid sequence represented by SEQ ID NO: 3 with Ala.

9. The protein of claim 1, wherein at least two of the polypeptide chains are contained.

10. A polynucleotide, encoding the immunoglobulin-binding protein of claim 1.

11. A vector, comprising the polynucleotide of claim 10.

12. A transformant, comprising the vector of claim 11.

13. An affinity carrier, comprising:
a solid carrier; and
the protein of claim 1, bound to the solid carrier.

14. A chromatography column, comprising:
the affinity carrier of claim 13.

15. A method for isolating an antibody or a fragment thereof, the method comprising:
contacting the antibody or the fragment with the affinity carrier of claim 13 or a chromatography column comprising the affinity carrier.

16. A method for producing an immunoglobulin-binding protein, the method comprising:
expressing the immunoglobulin-binding protein of claim 1 in a transformant comprising a vector comprising a polynucleotide, encoding the immunoglobulin-binding protein or a cell-free protein synthesis system, or chemically synthesizing the immunoglobulin-binding protein.

17. A method for producing a mutant polypeptide chain, the method comprising:
introducing at least one mutation into a polypeptide chain consisting of an amino acid sequence represented by at least 85% identity to any one of SEQ ID NOs: 1 to 6, 57 to 59 and 61-62, wherein the mutation is a substitution of Asn with Gln at a position corresponding to position 11 of the amino acid sequence represented by SEQ ID NO: 1, 2, 3, 5, or at position 6 of the amino acid sequence represented by SEQ ID No. 4, or at position 9 of the amino acid sequence represented by SEQ ID No. 6, or at position 7 of the amino acid sequence represented by SEQ ID No. 57, 58, 59, 61, 62 and optionally having at least one mutation selected from the group consisting of (a) to (f):
(a) substitution of an amino acid residue at at least one position selected from the group consisting of positions corresponding to positions 3 and 6 of the amino acid sequence represented by SEQ ID NO: 3 with another amino acid residue, deletion of the amino acid residue at the at least one position, or insertion of another amino acid residue into a position in front of or behind the at least one position;

(b) substitution of an amino acid residue at at least one position selected from the group consisting of positions corresponding to positions 24 and 25 of the amino acid sequence represented by SEQ ID NO: 3 with another amino acid residue, deletion of the amino acid residue at the at least one position, or insertion of another amino acid residue into a position in front of or behind the at least one position;

(c) substitution of an amino acid residue at a position corresponding to position 39 of the amino acid sequence represented by SEQ ID NO: 3 with another amino acid residue, deletion of the amino acid residue at the position corresponding to position 39, or insertion of another amino acid residue into a position in front of or behind the position corresponding to position 39;

(d) substitution of an amino acid residue at a position corresponding to position 46 of the amino acid sequence represented by SEQ ID NO: 3 with another amino acid residue, deletion of the amino acid residue at the position corresponding to position 46, or insertion of another amino acid residue into a position in front of or behind the position corresponding to position 46;

(e) substitution of an amino acid residue at at least one position selected from the group consisting of positions corresponding to positions 4, 49, and 58 of the amino acid sequence represented by SEQ ID NO: 3 with another amino acid residue, deletion of the amino acid residue at the at least one position, or insertion of another amino acid residue into a position in front of or behind the at least one position; and (f) substitution of an amino acid residue at a position corresponding to position 23 of the amino acid sequence represented by SEQ ID NO: 3 with another amino acid residue, deletion of the amino acid residue at the position corresponding to position 23, or insertion of another amino acid residue into a position in front of or behind the position corresponding to position 23.

18. A method for producing an affinity carrier, the method comprising:

immobilizing the immunoglobulin-binding protein of claim 1 on a solid carrier.

* * * * *

SEQUENCE LISTING

<160> NUMBER OF SEQ ID NOS: 62

<210> SEQ ID NO 1
<211> LENGTH: 58
<212> TYPE: PRT
<213> ORGANISM: Staphylococcus aureus
<220> FEATURE:
<223> OTHER INFORMATION: Protein A, B domain

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Staphylococcus aureus
<220> FEATURE:
<223> OTHER INFORMATION: Protein A, Z domain

<400> SEQUENCE: 2

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
         50                  55

<210> SEQ ID NO 3
<211> LENGTH: 58
<212> TYPE: PRT
<213> ORGANISM: Staphylococcus aureus
<220> FEATURE:
<223> OTHER INFORMATION: Protein A, C domain

<400> SEQUENCE: 3

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
         20                  25                  30

Ser Leu Lys Asp Asp Pro Ser Val Ser Lys Glu Ile Leu Ala Glu Ala
         35                  40                  45

Lys Lys Leu Asn Asp Ala Gln Ala Pro Lys
         50                  55

<210> SEQ ID NO 4
<211> LENGTH: 61
<212> TYPE: PRT
<213> ORGANISM: Staphylococcus aureus
<220> FEATURE:
<223> OTHER INFORMATION: Protein A, D domain

<400> SEQUENCE: 4

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
         20                  25                  30

Phe Ile Gln Ser Leu Lys Asp Asp Pro Ser Gln Ser Thr Asn Val Leu
         35                  40                  45

Gly Glu Ala Lys Lys Leu Asn Glu Ser Gln Ala Pro Lys
         50                  55                  60

<210> SEQ ID NO 5
<211> LENGTH: 58
<212> TYPE: PRT
<213> ORGANISM: Staphylococcus aureus
<220> FEATURE:
<223> OTHER INFORMATION: Protein A, A domain

<400> SEQUENCE: 5

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
         20                  25                  30

Ser Leu Lys Asp Asp Pro Ser Gln Ser Ala Asn Leu Leu Ser Glu Ala
         35                  40                  45

Lys Lys Leu Asn Glu Ser Gln Ala Pro Lys
         50                  55

<210> SEQ ID NO 6
<211> LENGTH: 56
<212> TYPE: PRT
<213> ORGANISM: Staphylococcus aureus
<220> FEATURE:
<223> OTHER INFORMATION: Protein A, E domain

```
<400> SEQUENCE: 6

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 7
<211> LENGTH: 58
<212> TYPE: PRT
<213> ORGANISM: Staphylococcus aureus
<220> FEATURE:
<223> OTHER INFORMATION: N3Q variant domain

<400> SEQUENCE: 7

Val Asp Gln Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 8
<211> LENGTH: 57
<212> TYPE: PRT
<213> ORGANISM: Staphylococcus aureus
<220> FEATURE:
<223> OTHER INFORMATION: delta-K4 variant domain

<400> SEQUENCE: 8

Val Asp Asn Phe Asn Lys Glu Gln Gln Asn Ala Phe Tyr Glu Ile Leu
1               5                   10                  15

His Leu Pro Asn Leu Thr Glu Glu Gln Arg Asn Ala Phe Ile Gln Ser
            20                  25                  30

Leu Lys Asp Asp Pro Ser Val Ser Lys Glu Ile Leu Ala Glu Ala Lys
        35                  40                  45

Lys Leu Asn Asp Ala Gln Ala Pro Lys
    50                  55

<210> SEQ ID NO 9
<211> LENGTH: 58
<212> TYPE: PRT
<213> ORGANISM: Staphylococcus aureus
<220> FEATURE:
<223> OTHER INFORMATION: N6Q variant domain

<400> SEQUENCE: 9

Val Asp Asn Lys Phe Gln Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
```

<210> SEQ ID NO 10
<211> LENGTH: 58
<212> TYPE: PRT
<213> ORGANISM: Staphylococcus aureus
<220> FEATURE:
<223> OTHER INFORMATION: N11Q variant domain

<400> SEQUENCE: 10

Val Asp Asn Lys Phe Asn Lys Glu Gln Gln Gln Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Staphylococcus aureus
<220> FEATURE:
<223> OTHER INFORMATION: N3Q, N6Q, N11Q variant domain

<400> SEQUENCE: 11

Val Asp Gln Lys Phe Gln Lys Glu Gln Gln Gln Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 12
<211> LENGTH: 58
<212> TYPE: PRT
<213> ORGANISM: Staphylococcus aureus
<220> FEATURE:
<223> OTHER INFORMATION: E24D variant domain

<400> SEQUENCE: 12

Val Asp Asn Lys Phe Asn Lys Glu Gln Gln Asn Ala Phe Tyr Glu Ile
1               5                   10                  15

Leu His Leu Pro Asn Leu Thr Asp Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 13
<211> LENGTH: 58
<212> TYPE: PRT
<213> ORGANISM: Staphylococcus aureus
<220> FEATURE:
<223> OTHER INFORMATION: E25D variant domain

<400> SEQUENCE: 13

Val Asp Asn Lys Phe Asn Lys Glu Gln Gln Asn Ala Phe Tyr Glu Ile

```
                1               5                  10                 15
Leu His Leu Pro Asn Leu Thr Glu Asp Gln Arg Asn Ala Phe Ile Gln
                20                  25                 30

Ser Leu Lys Asp Asp Pro Ser Val Ser Lys Glu Ile Leu Ala Glu Ala
            35                  40                 45

Lys Lys Leu Asn Asp Ala Gln Ala Pro Lys
        50                  55

<210> SEQ ID NO 14
<211> LENGTH: 58
<212> TYPE: PRT
<213> ORGANISM: Staphylococcus aureus
<220> FEATURE:
<223> OTHER INFORMATION: S39K variant domain

<400> SEQUENCE: 14

Val Asp Asn Lys Phe Asn Lys Glu Gln Gln Asn Ala Phe Tyr Glu Ile
1               5                  10                 15

Leu His Leu Pro Asn Leu Thr Glu Glu Gln Arg Asn Ala Phe Ile Gln
                20                  25                 30

Ser Leu Lys Asp Asp Pro Lys Val Ser Lys Glu Ile Leu Ala Glu Ala
            35                  40                 45

Lys Lys Leu Asn Asp Ala Gln Ala Pro Lys
        50                  55

<210> SEQ ID NO 15
<211> LENGTH: 58
<212> TYPE: PRT
<213> ORGANISM: Staphylococcus aureus
<220> FEATURE:
<223> OTHER INFORMATION: S39R variant domain

<400> SEQUENCE: 15

Val Asp Asn Lys Phe Asn Lys Glu Gln Gln Asn Ala Phe Tyr Glu Ile
1               5                  10                 15

Leu His Leu Pro Asn Leu Thr Glu Glu Gln Arg Asn Ala Phe Ile Gln
                20                  25                 30

Ser Leu Lys Asp Asp Pro Arg Val Ser Lys Glu Ile Leu Ala Glu Ala
            35                  40                 45

Lys Lys Leu Asn Asp Ala Gln Ala Pro Lys
        50                  55

<210> SEQ ID NO 16
<211> LENGTH: 58
<212> TYPE: PRT
<213> ORGANISM: Staphylococcus aureus
<220> FEATURE:
<223> OTHER INFORMATION: A46D variant domain

<400> SEQUENCE: 16

Val Asp Asn Lys Phe Asn Lys Glu Gln Gln Asn Ala Phe Tyr Glu Ile
1               5                  10                 15

Leu His Leu Pro Asn Leu Thr Glu Glu Gln Arg Asn Ala Phe Ile Gln
                20                  25                 30

Ser Leu Lys Asp Asp Pro Ser Val Ser Lys Glu Ile Leu Asp Glu Ala
            35                  40                 45

Lys Lys Leu Asn Asp Ala Gln Ala Pro Lys
        50                  55

<210> SEQ ID NO 17
```

-continued

<211> LENGTH: 58
<212> TYPE: PRT
<213> ORGANISM: Staphylococcus aureus
<220> FEATURE:
<223> OTHER INFORMATION: A46E variant domain

<400> SEQUENCE: 17

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Glu Glu Ala
        35                  40                  45

Lys Lys Leu Asn Asp Ala Gln Ala Pro Lys
    50                  55

<210> SEQ ID NO 18
<211> LENGTH: 58
<212> TYPE: PRT
<213> ORGANISM: Staphylococcus aureus
<220> FEATURE:
<223> OTHER INFORMATION: A46K variant domain

<400> SEQUENCE: 18

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Lys Glu Ala
        35                  40                  45

Lys Lys Leu Asn Asp Ala Gln Ala Pro Lys
    50                  55

<210> SEQ ID NO 19
<211> LENGTH: 58
<212> TYPE: PRT
<213> ORGANISM: Staphylococcus aureus
<220> FEATURE:
<223> OTHER INFORMATION: A46R variant domain

<400> SEQUENCE: 19

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Arg Glu Ala
        35                  40                  45

Lys Lys Leu Asn Asp Ala Gln Ala Pro Lys
    50                  55

<210> SEQ ID NO 20
<211> LENGTH: 58
<212> TYPE: PRT
<213> ORGANISM: Staphylococcus aureus
<220> FEATURE:
<223> OTHER INFORMATION: K49R variant domain

<400> SEQUENCE: 20

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
            35                  40                  45

Arg Lys Leu Asn Asp Ala Gln Ala Pro Lys
        50                  55

<210> SEQ ID NO 21
<211> LENGTH: 58
<212> TYPE: PRT
<213> ORGANISM: Staphylococcus aureus
<220> FEATURE:
<223> OTHER INFORMATION: K58R variant domain

<400> SEQUENCE: 21

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Arg
        50                  55

<210> SEQ ID NO 22
<211> LENGTH: 57
<212> TYPE: PRT
<213> ORGANISM: Staphylococcus aureus
<220> FEATURE:
<223> OTHER INFORMATION: delta-K58 variant domain

<400> SEQUENCE: 22

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro
        50                  55

<210> SEQ ID NO 23
<211> LENGTH: 58
<212> TYPE: PRT
<213> ORGANISM: Staphylococcus aureus
<220> FEATURE:
<223> OTHER INFORMATION: N3A, N11Q variant domain

<400> SEQUENCE: 23

Val Asp Ala Lys Phe Asn Lys Glu Gln Gln Gln Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys
        50                  55

<210> SEQ ID NO 24
<211> LENGTH: 58
<212> TYPE: PRT
<213> ORGANISM: Staphylococcus aureus
<220> FEATURE:

<223> OTHER INFORMATION: N3D, N11Q variant domain

<400> SEQUENCE: 24

Val Asp Asp Lys Phe Asn Lys Glu Gln Gln Gln Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 25
<211> LENGTH: 58
<212> TYPE: PRT
<213> ORGANISM: Staphylococcus aureus
<220> FEATURE:
<223> OTHER INFORMATION: N6D, N11Q variant domain

<400> SEQUENCE: 25

Val Asp Asn Lys Phe Asp Lys Glu Gln Gln Gln Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 26
<211> LENGTH: 58
<212> TYPE: PRT
<213> ORGANISM: Staphylococcus aureus
<220> FEATURE:
<223> OTHER INFORMATION: N3D, N6D, N11Q variant domain

<400> SEQUENCE: 26

Val Asp Asp Lys Phe Asp Lys Glu Gln Gln Gln Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 27
<211> LENGTH: 58
<212> TYPE: PRT
<213> ORGANISM: Staphylococcus aureus
<220> FEATURE:
<223> OTHER INFORMATION: N3A, N6D, N11Q variant domain

<400> SEQUENCE: 27

Val Asp Ala Lys Phe Asp Lys Glu Gln Gln Gln Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 28
<211> LENGTH: 58
<212> TYPE: PRT
<213> ORGANISM: Staphylococcus aureus
<220> FEATURE:
<223> OTHER INFORMATION: N11Q, T23R variant domain

<400> SEQUENCE: 28

Val Asp Asn Lys Phe Asn Lys Glu Gln Gln Gln Ala Phe Tyr Glu Ile
1               5                   10                  15

Leu His Leu Pro Asn Leu Arg Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 29
<211> LENGTH: 58
<212> TYPE: PRT
<213> ORGANISM: Staphylococcus aureus
<220> FEATURE:
<223> OTHER INFORMATION: N11Q, T23L variant domain

<400> SEQUENCE: 29

Val Asp Asn Lys Phe Asn Lys Glu Gln Gln Gln Ala Phe Tyr Glu Ile
1               5                   10                  15

Leu His Leu Pro Asn Leu Leu Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 30
<211> LENGTH: 58
<212> TYPE: PRT
<213> ORGANISM: Staphylococcus aureus
<220> FEATURE:
<223> OTHER INFORMATION: N11Q, T23S variant domain

<400> SEQUENCE: 30

Val Asp Asn Lys Phe Asn Lys Glu Gln Gln Gln Ala Phe Tyr Glu Ile
1               5                   10                  15

Leu His Leu Pro Asn Leu Ser Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 31
<211> LENGTH: 58
<212> TYPE: PRT
<213> ORGANISM: Staphylococcus aureus
<220> FEATURE:
<223> OTHER INFORMATION: N11Q, K49R variant domain

<400> SEQUENCE: 31

-continued

```
Val Asp Asn Lys Phe Asn Lys Glu Gln Gln Gln Ala Phe Tyr Glu Ile
 1               5                  10                  15

Leu His Leu Pro Asn Leu Thr Glu Glu Gln Arg Asn Ala Phe Ile Gln
             20                  25                  30

Ser Leu Lys Asp Asp Pro Ser Val Ser Lys Glu Ile Leu Ala Glu Ala
         35                  40                  45

Arg Lys Leu Asn Asp Ala Gln Ala Pro Lys
     50                  55
```

<210> SEQ ID NO 32
<211> LENGTH: 58
<212> TYPE: PRT
<213> ORGANISM: Staphylococcus aureus
<220> FEATURE:
<223> OTHER INFORMATION: N11Q, T23R, K49R variant domain

<400> SEQUENCE: 32

```
Val Asp Asn Lys Phe Asn Lys Glu Gln Gln Gln Ala Phe Tyr Glu Ile
 1               5                  10                  15

Leu His Leu Pro Asn Leu Arg Glu Glu Gln Arg Asn Ala Phe Ile Gln
             20                  25                  30

Ser Leu Lys Asp Asp Pro Ser Val Ser Lys Glu Ile Leu Ala Glu Ala
         35                  40                  45

Arg Lys Leu Asn Asp Ala Gln Ala Pro Lys
     50                  55
```

<210> SEQ ID NO 33
<211> LENGTH: 58
<212> TYPE: PRT
<213> ORGANISM: Staphylococcus aureus
<220> FEATURE:
<223> OTHER INFORMATION: N11Q, T23L, K49R variant domain

<400> SEQUENCE: 33

```
Val Asp Asn Lys Phe Asn Lys Glu Gln Gln Gln Ala Phe Tyr Glu Ile
 1               5                  10                  15

Leu His Leu Pro Asn Leu Leu Glu Glu Gln Arg Asn Ala Phe Ile Gln
             20                  25                  30

Ser Leu Lys Asp Asp Pro Ser Val Ser Lys Glu Ile Leu Ala Glu Ala
         35                  40                  45

Arg Lys Leu Asn Asp Ala Gln Ala Pro Lys
     50                  55
```

<210> SEQ ID NO 34
<211> LENGTH: 58
<212> TYPE: PRT
<213> ORGANISM: Staphylococcus aureus
<220> FEATURE:
<223> OTHER INFORMATION: N11Q, T23S, K49R variant domain

<400> SEQUENCE: 34

```
Val Asp Asn Lys Phe Asn Lys Glu Gln Gln Gln Ala Phe Tyr Glu Ile
 1               5                  10                  15

Leu His Leu Pro Asn Leu Ser Glu Glu Gln Arg Asn Ala Phe Ile Gln
             20                  25                  30

Ser Leu Lys Asp Asp Pro Ser Val Ser Lys Glu Ile Leu Ala Glu Ala
         35                  40                  45

Arg Lys Leu Asn Asp Ala Gln Ala Pro Lys
     50                  55
```

-continued

```
<210> SEQ ID NO 35
<211> LENGTH: 58
<212> TYPE: PRT
<213> ORGANISM: Staphylococcus aureus
<220> FEATURE:
<223> OTHER INFORMATION: N11Q, K58R variant domain

<400> SEQUENCE: 35

Val Asp Asn Lys Phe Asn Lys Glu Gln Gln Gln Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Arg
    50                  55

<210> SEQ ID NO 36
<211> LENGTH: 58
<212> TYPE: PRT
<213> ORGANISM: Staphylococcus aureus
<220> FEATURE:
<223> OTHER INFORMATION: T23R variant domain

<400> SEQUENCE: 36

Val Asp Asn Lys Phe Asn Lys Glu Gln Gln Asn Ala Phe Tyr Glu Ile
1               5                   10                  15

Leu His Leu Pro Asn Leu Arg Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 37
<211> LENGTH: 58
<212> TYPE: PRT
<213> ORGANISM: Staphylococcus aureus
<220> FEATURE:
<223> OTHER INFORMATION: T23L variant domain

<400> SEQUENCE: 37

Val Asp Asn Lys Phe Asn Lys Glu Gln Gln Asn Ala Phe Tyr Glu Ile
1               5                   10                  15

Leu His Leu Pro Asn Leu Leu Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 38
<211> LENGTH: 58
<212> TYPE: PRT
<213> ORGANISM: Staphylococcus aureus
<220> FEATURE:
<223> OTHER INFORMATION: T23S variant domain

<400> SEQUENCE: 38

Val Asp Asn Lys Phe Asn Lys Glu Gln Gln Asn Ala Phe Tyr Glu Ile
1               5                   10                  15

Leu His Leu Pro Asn Leu Ser Glu Glu Gln Arg Asn Ala Phe Ile Gln
```

```
                20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 39
<211> LENGTH: 58
<212> TYPE: PRT
<213> ORGANISM: Staphylococcus aureus
<220> FEATURE:
<223> OTHER INFORMATION: N11A variant domain

<400> SEQUENCE: 39

Val Asp Asn Lys Phe Asn Lys Glu Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 40
<211> LENGTH: 58
<212> TYPE: PRT
<213> ORGANISM: Staphylococcus aureus
<220> FEATURE:
<223> OTHER INFORMATION: N11R variant domain

<400> SEQUENCE: 40

Val Asp Asn Lys Phe Asn Lys Glu Gln Gln Arg Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 41
<211> LENGTH: 58
<212> TYPE: PRT
<213> ORGANISM: Staphylococcus aureus
<220> FEATURE:
<223> OTHER INFORMATION: N11D variant domain

<400> SEQUENCE: 41

Val Asp Asn Lys Phe Asn Lys Glu Gln Gln Asp Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 42
<211> LENGTH: 58
<212> TYPE: PRT
<213> ORGANISM: Staphylococcus aureus
```

```
<220> FEATURE:
<223> OTHER INFORMATION: N11C variant domain

<400> SEQUENCE: 42

Val Asp Asn Lys Phe Asn Lys Glu Gln Gln Cys Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 43
<211> LENGTH: 58
<212> TYPE: PRT
<213> ORGANISM: Staphylococcus aureus
<220> FEATURE:
<223> OTHER INFORMATION: N11E variant domain

<400> SEQUENCE: 43

Val Asp Asn Lys Phe Asn Lys Glu Gln Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 44
<211> LENGTH: 58
<212> TYPE: PRT
<213> ORGANISM: Staphylococcus aureus
<220> FEATURE:
<223> OTHER INFORMATION: N11H variant domain

<400> SEQUENCE: 44

Val Asp Asn Lys Phe Asn Lys Glu Gln Gln His Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 45
<211> LENGTH: 58
<212> TYPE: PRT
<213> ORGANISM: Staphylococcus aureus
<220> FEATURE:
<223> OTHER INFORMATION: N11I variant domain

<400> SEQUENCE: 45

Val Asp Asn Lys Phe Asn Lys Glu Gln Gln Ile Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45
```

-continued

```
Lys Lys Leu Asn Asp Ala Gln Ala Pro Lys
    50                  55

<210> SEQ ID NO 46
<211> LENGTH: 58
<212> TYPE: PRT
<213> ORGANISM: Staphylococcus aureus
<220> FEATURE:
<223> OTHER INFORMATION: N11L variant domain

<400> SEQUENCE: 46

Val Asp Asn Lys Phe Asn Lys Glu Gln Gln Leu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 47
<211> LENGTH: 58
<212> TYPE: PRT
<213> ORGANISM: Staphylococcus aureus
<220> FEATURE:
<223> OTHER INFORMATION: N11K variant domain

<400> SEQUENCE: 47

Val Asp Asn Lys Phe Asn Lys Glu Gln Gln Lys Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 48
<211> LENGTH: 58
<212> TYPE: PRT
<213> ORGANISM: Staphylococcus aureus
<220> FEATURE:
<223> OTHER INFORMATION: N11M variant domain

<400> SEQUENCE: 48

Val Asp Asn Lys Phe Asn Lys Glu Gln Gln Met Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 49
<211> LENGTH: 58
<212> TYPE: PRT
<213> ORGANISM: Staphylococcus aureus
<220> FEATURE:
<223> OTHER INFORMATION: N11F variant domain

<400> SEQUENCE: 49
```

Val Asp Asn Lys Phe Asn Lys Glu Gln Gln Phe Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 50
<211> LENGTH: 58
<212> TYPE: PRT
<213> ORGANISM: Staphylococcus aureus
<220> FEATURE:
<223> OTHER INFORMATION: N11T variant domain

<400> SEQUENCE: 50

Val Asp Asn Lys Phe Asn Lys Glu Gln Gln Thr Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 51
<211> LENGTH: 58
<212> TYPE: PRT
<213> ORGANISM: Staphylococcus aureus
<220> FEATURE:
<223> OTHER INFORMATION: N11W variant domain

<400> SEQUENCE: 51

Val Asp Asn Lys Phe Asn Lys Glu Gln Gln Trp Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 52
<211> LENGTH: 58
<212> TYPE: PRT
<213> ORGANISM: Staphylococcus aureus
<220> FEATURE:
<223> OTHER INFORMATION: N11Y variant domain

<400> SEQUENCE: 52

Val Asp Asn Lys Phe Asn Lys Glu Gln Gln Tyr Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 53
<211> LENGTH: 58
<212> TYPE: PRT
<213> ORGANISM: Staphylococcus aureus
<220> FEATURE:
<223> OTHER INFORMATION: N11V variant domain

<400> SEQUENCE: 53

```
Val Asp Asn Lys Phe Asn Lys Glu Gln Gln Val Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 54
<211> LENGTH: 58
<212> TYPE: PRT
<213> ORGANISM: Staphylococcus aureus
<220> FEATURE:
<223> OTHER INFORMATION: N11G variant domain

<400> SEQUENCE: 54

```
Val Asp Asn Lys Phe Asn Lys Glu Gln Gln Gly Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 55
<211> LENGTH: 58
<212> TYPE: PRT
<213> ORGANISM: Staphylococcus aureus
<220> FEATURE:
<223> OTHER INFORMATION: N11P variant domain

<400> SEQUENCE: 55

```
Val Asp Asn Lys Phe Asn Lys Glu Gln Gln Pro Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 56
<211> LENGTH: 58
<212> TYPE: PRT
<213> ORGANISM: Staphylococcus aureus
<220> FEATURE:
<223> OTHER INFORMATION: N11S variant domain

<400> SEQUENCE: 56

```
Val Asp Asn Lys Phe Asn Lys Glu Gln Gln Ser Ala Phe Tyr Glu Ile
1               5                   10                  15
```

```
Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 57
<211> LENGTH: 54
<212> TYPE: PRT
<213> ORGANISM: Staphylococcus aureus
<220> FEATURE:
<223> OTHER INFORMATION: Protein A, B domain variant

<400> SEQUENCE: 57

Phe Asn Lys Glu Gln Gln Asn Ala Phe Tyr Glu Ile Leu His Leu Pro
1               5                   10                  15

Asn Leu Asn Glu Glu Gln Arg Asn Gly Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys
    50

<210> SEQ ID NO 58
<211> LENGTH: 54
<212> TYPE: PRT
<213> ORGANISM: Staphylococcus aureus
<220> FEATURE:
<223> OTHER INFORMATION: Protein A, Z domain variant

<400> SEQUENCE: 58

Phe Asn Lys Glu Gln Gln Asn Ala Phe Tyr Glu Ile Leu His Leu Pro
1               5                   10                  15

Asn Leu Asn Glu Glu Gln Arg Asn Ala Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys
    50

<210> SEQ ID NO 59
<211> LENGTH: 54
<212> TYPE: PRT
<213> ORGANISM: Staphylococcus aureus
<220> FEATURE:
<223> OTHER INFORMATION: Protein A, C domain variant

<400> SEQUENCE: 59

Phe Asn Lys Glu Gln Gln Asn Ala Phe Tyr Glu Ile Leu His Leu Pro
1               5                   10                  15

Asn Leu Thr Glu Glu Gln Arg Asn Gly Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys
    50

<210> SEQ ID NO 60
<211> LENGTH: 54
<212> TYPE: PRT
```

```
<213> ORGANISM: Staphylococcus aureus
<220> FEATURE:
<223> OTHER INFORMATION: Protein A, D domain variant

<400> SEQUENCE: 60

Phe Asn Lys Asp Gln Gln Ser Ala Phe Tyr Glu Ile Leu Asn Met Pro
1               5                   10                  15

Asn Leu Asn Glu Ala Gln Arg Asn Gly Phe Ile Gln Ser Leu Lys Asp
            20                  25                  30

Asp Pro Ser Gln Ser Thr Asn Val Leu Gly Glu Ala Lys Lys Leu Asn
        35                  40                  45

Glu Ser Gln Ala Pro Lys
    50

<210> SEQ ID NO 61
<211> LENGTH: 54
<212> TYPE: PRT
<213> ORGANISM: Staphylococcus aureus
<220> FEATURE:
<223> OTHER INFORMATION: Protein A, A domain variant

<400> SEQUENCE: 61

Phe Asn Lys Glu Gln Gln Asn Ala Phe Tyr Glu Ile Leu Asn Met Pro
1               5                   10                  15

Asn Leu Asn Glu Glu Gln Arg Asn Gly Phe Ile Gln Ser Leu Lys Asp
            20                  25                  30

Asp Pro Ser Gln Ser Ala Asn Leu Leu Ser Glu Ala Lys Lys Leu Asn
        35                  40                  45

Glu Ser Gln Ala Pro Lys
    50

<210> SEQ ID NO 62
<211> LENGTH: 54
<212> TYPE: PRT
<213> ORGANISM: Staphylococcus aureus
<220> FEATURE:
<223> OTHER INFORMATION: Protein A, E domain variant

<400> SEQUENCE: 62

His Asp Glu Ala Gln Gln Asn Ala Phe Tyr Gln Val Leu Asn Met Pro
1               5                   10                  15

Asn Leu Asn Ala Asp Gln Arg Asn Gly Phe Ile Gln Ser Leu Lys Asp
            20                  25                  30

Asp Pro Ser Gln Ser Ala Asn Val Leu Gly Glu Ala Gln Lys Leu Asn
        35                  40                  45

Asp Ser Gln Ala Pro Lys
    50
```